(12) United States Patent
Liu et al.

(10) Patent No.: US 11,531,017 B2
(45) Date of Patent: Dec. 20, 2022

(54) METHOD FOR ASSESSING WATER SHORTAGE RISK, DEVICE, COMPUTER DEVICE AND STORAGE MEDIUM

(71) Applicant: SOUTHERN UNIVERSITY OF SCIENCE AND TECHNOLOGY, Shenzhen (CN)

(72) Inventors: Junguo Liu, Shenzhen (CN); Ganquan Mao, Shenzhen (CN)

(*) Notice: Subject to any disclaimer, the term of this patent is extended or adjusted under 35 U.S.C. 154(b) by 356 days.

(21) Appl. No.: 16/937,554

(22) Filed: Jul. 23, 2020

(65) Prior Publication Data

US 2021/0018484 A1    Jan. 21, 2021

(30) Foreign Application Priority Data

May 24, 2019    (CN) .......................... 201910439661.7

(51) Int. Cl.
| | |
|---|---|
| *G01N 33/24* | (2006.01) |
| *G06F 30/20* | (2020.01) |
| *A01G 25/16* | (2006.01) |
| *E02B 13/00* | (2006.01) |

(52) U.S. Cl.
CPC ........... *G01N 33/246* (2013.01); *A01G 25/16* (2013.01); *E02B 13/00* (2013.01); *G06F 30/20* (2020.01); *G01N 2033/245* (2013.01)

(58) Field of Classification Search
CPC ........... G01N 33/246; G01N 2033/245; A01G 25/16; E02B 13/00; G06F 30/20; G06Q 10/0635; G06Q 10/0639; G06Q 50/06
See application file for complete search history.

(56) References Cited

U.S. PATENT DOCUMENTS

| | | | |
|---|---|---|---|
| 2016/0309646 A1* | 10/2016 | Starr | A01C 21/007 |
| 2019/0230875 A1* | 8/2019 | Mewes | A01G 25/167 |
| 2021/0145008 A1* | 5/2021 | Bais | A01N 63/22 |

* cited by examiner

*Primary Examiner* — Chad G Erdman

(57) ABSTRACT

In the present application, a method for assessing water shortage risk, device, computer device and storage medium are provided, wherein the method for assessing water shortage risk comprises: acquiring a volume of blue water flowing into soil of a to-be-assessed-area within a target time period, and a volume of retention water flowing into and retained in the soil of the to-be-assessed-area within the target time period; and determining a water shortage risk indicator of the to-be-assessed-area indicating a degree of water shortage risk of the to-be-assessed-area, according to a ratio of the volume of blue water to the volume of retention water. A higher ratio of the volume of blue water to the volume of retention water indicates poor ability of the soil's water to meet the demand for use and greater degree of the water shortage risk of the soil.

20 Claims, 18 Drawing Sheets performing ecological hydrological simulation with an ecological hydrological model, to obtain a simulation result comprising the volume of blue water, a volume of outflow water flowing out of soil in the to-be-assessed-area and a volume of vegetation retention water within the target time period — S301 obtaining the volume of retention water according to precipitation, the volume of vegetation retention water, the volume of blue water and the volume of outflow water within the target time period — S302

FIG. 5

1. precipitation
4. subsurface flow
7. channel leakage
0. vegetation retention
3. surface runoff
5. groundwater supplied
8. capillary water
6. irrigation

US 11,531,017 B2

METHOD FOR ASSESSING WATER SHORTAGE RISK, DEVICE, COMPUTER DEVICE AND STORAGE MEDIUM

CROSS REFERENCE TO RELATED APPLICATIONS

This application claims priority to Chinese Patent Application No. 201910439661.7, filed on May 24, 2019, the entire contents of which are incorporated herein by reference.

TECHNICAL FIELD

The present application relates to the technical field of water conservancy, especially relates to a method for assessing water shortage risk, device, computer device and storage media.

BACKGROUND

Facing the reality of the increasing shortage of water resources in the world, analyzing and evaluating the water shortage risk in a certain area is the basic work for rational development, utilization, protection and management of water resources, and can provide a basis for water conservancy planning.

The water shortage risk assessment is to analyze the water supply level of a region, mainly according to the water resources stored in rivers, lakes and underground aquifers and the amount of precipitation in a region, and the water demand for human activities, such as recycled water, agricultural water consumption, industrial water consumption, and water for the third industry and domestic use, for assessment of water shortage risk in this area, and to determine whether there is a water shortage risk in the region by assessing the relationship between the amount of water available to human activities and the water demand by human activities.

However, the above method for assessing the water shortage risk has the problem of incomplete assessment results.

SUMMARY

Based on this, it is necessary to provide a method for assessing water shortage risk, device, computer device and storage media for solving the problem of incomplete assessment results for the above water shortage risk assessment method.

In a first aspect, an embodiment of the present application provides a method for assessing water shortage risk, comprising:

acquiring a volume of blue water flowing into soil of a to-be-assessed-area within a target time period, and a volume of retention water flowing into and retained in the soil of the to-be-assessed-area within the target time period; and determining a water shortage risk indicator of the to-be-assessed-area indicating a degree of water shortage risk of the to-be-assessed-area, according to a ratio of the volume of blue water to the volume of retention water.

In a second aspect, an embodiment of the present application provides a water shortage risk assessment device, comprising:

an acquisition module, for acquiring a volume of blue water flowing into soil of a to-be-assessed-area within a target time period, and a volume of retention water flowing into and retained in the soil of the to-be-assessed-area within the target time period; and an indicator determination module, for determining a water shortage risk indicator of the to-be-assessed-area indicating a degree of water shortage risk of the to-be-assessed-area, according to a ratio of the volume of blue water to the volume of retention water.

In a third aspect, an embodiment of the present application provides a computer device, comprising memory storing computer programs and a processor, wherein, the processor, when executing the computer program, realizes the method for assessing water shortage risk in the first aspect.

In a fourth aspect, an embodiment of the present application provides a computer readable storage medium, storing computer program thereon, wherein, the computer program, when executed by the processor, realizes the method for assessing water shortage risk in the first aspect.

According to the method for assessing water shortage risk, device, computer device and storage medium provided in the above embodiments, a water shortage risk indicator of the to-be-assessed-area is determined according to a ratio of the volume of blue water flowing into soil of a to-be-assessed-area to the volume of retention water flowing into and retained in the soil of the to-be-assessed-area, and because the volume of blue water can indicate the volume of blue water available to soil in the to-be-assessed-area, the volume of retention water can indicate the total volume of water available to soil in the to-be-assessed-area, thus the ratio of the volume of blue water to the volume of retention water can indicate the degree of demand of soil for the blue water, the greater the ratio, the greater the demand the soil has for the volume of blue water, i.e., the lower the degree the water in the soil meets the requirements for use, the greater the degree of water shortage risk for the soil. Therefore, in the present application, the demand of the soil for the volume of blue water is taken into account when the water shortage risk indicator of to-be-assessed-area is determined, so that the determined water shortage risk indicator can indicate the extent of water shortage risk in the ecological environment, improving comprehensiveness in comparison with the method to determine whether there is a risk of water shortage in the area merely according to the relationship between the available water amount that can be provided to human production activities and the water demand of human activities in an area in related technology.

BRIEF DESCRIPTION OF THE DRAWINGS

FIG. 5 is a flowchart of a method for assessing water shortage risk which provided in a further embodiment;

DETAILED DESCRIPTION

In order to make a more clear description of the purpose, technical solution and advantages of the present application, the present application will be described in further detail in conjunction with drawings and embodiments. It should be understood that the specific embodiments described herein are only used to explain the present application, rather than impose limitation on the present application.

It should be noted that terms such as "first", "second", "third" and "fourth" in the description, claim and the above drawings of the present application are used to distinguish similar objects, not necessarily to describe specific order or sequence. It should be understood that the data used in this way can be interchanged under appropriate circumstances, so that embodiments of the present application described can be implemented in an order other than those illustrated or described herein. In addition, terms such as "comprising" and "provided with" and any variations thereof are intended to cover non-exclusive inclusions, for example, comprise processes, methods, systems, products or equipment that contain a series of steps or units need not be limited to those steps or units that are clearly listed, but may include other steps or units that are not clearly listed but inherent to these processes, methods, products or equipment.

Figure 1:
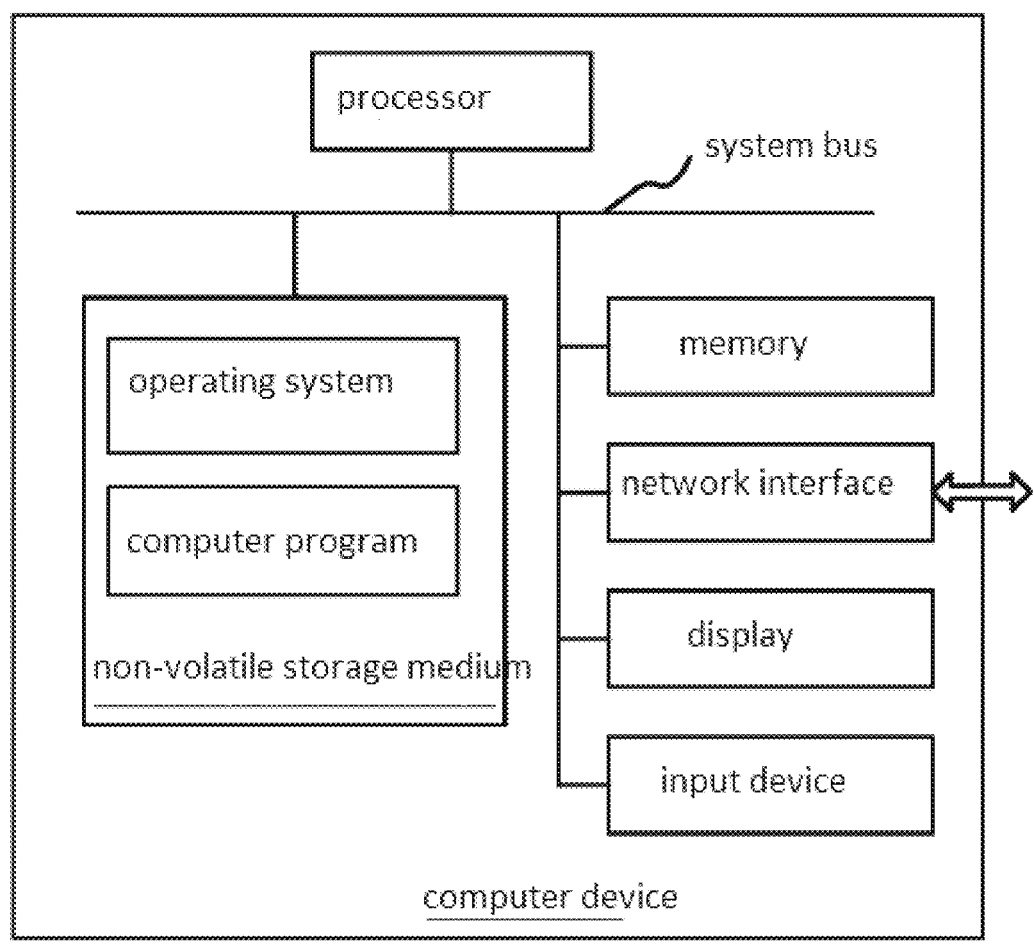
FIG. 1 is a schematic diagram of the internal structure of a computer device provided in an embodiment.

A method for assessing water shortage risk is provided in an embodiment of the present application, and can be applied to the computer device shown in FIG. 1, which can be a terminal or a server, and in the case that the terminal is the computer device, the internal structure of the computer device is shown in FIG. 1. The computer device includes a processor, memory, network interface, display and input device connected through a system bus. Among them, the processor of the computer device is used to provide computing and control capabilities. The memory of the computer device includes non-volatile storage medium and internal memory. The non-volatile storage medium stores an operating system and computer program. The internal memory provides environment for operation of the operating system and computer program in the non-volatile storage medium. The network interface of the computer device is used to communicate with external terminals through network links. The computer program, when executed by the processor, implements the steps of method for assessing water shortage risk. The computer device may include a liquid crystal display or an electronic ink display, and the input device of the computer device may be a touch layer covered on the display, and can also be a button, trackball or touchpad provided on the computer device shell, or an external keyboard, touchpad or mouse.

Those killed in the art can understand that the structure shown in FIG. 1 is only a block diagram of a part of the structure related to the solution of the present application, and does not constitute a limitation on the computer device to which the solution of the present application is applied. Specific computer device may include more or fewer parts than shown in the drawings, or a combination of certain components, or different arrangement of the components.

At present, the most commonly used method for water shortage risk assessment is the average per capita water resource analysis method, which is to average a total volume of blue water resource and total population in an area (river basin) during a certain period, to determine the amount of water resources for each person, so as to judge the risk of water shortage in the area (river basin), for which there is a problem of incomplete evaluation results, for example, the blue water resource is preferentially allocated to human activities, while a small amount of the blue water resource is allocated to the ecological environment, resulting into a situation where human society does not lack water, but the ecological environment is short of water. In the present application, the demand of soil for the volume of blue water is taken into account, when the water shortage risk indicator of to-be-assessed-area is determined, so that the determined water shortage risk indicator can indicate the degree of water shortage risk in the ecological environment, improving comprehensiveness. The technical solution of the present application and how the technical solution of the present application solves the above technical problems will be explained in detail as follows through embodiments in combination with the drawings. The following embodiments can be combined with each other, and the same or similar concepts or processes may not be repeated in some embodiments.

Figure 2:
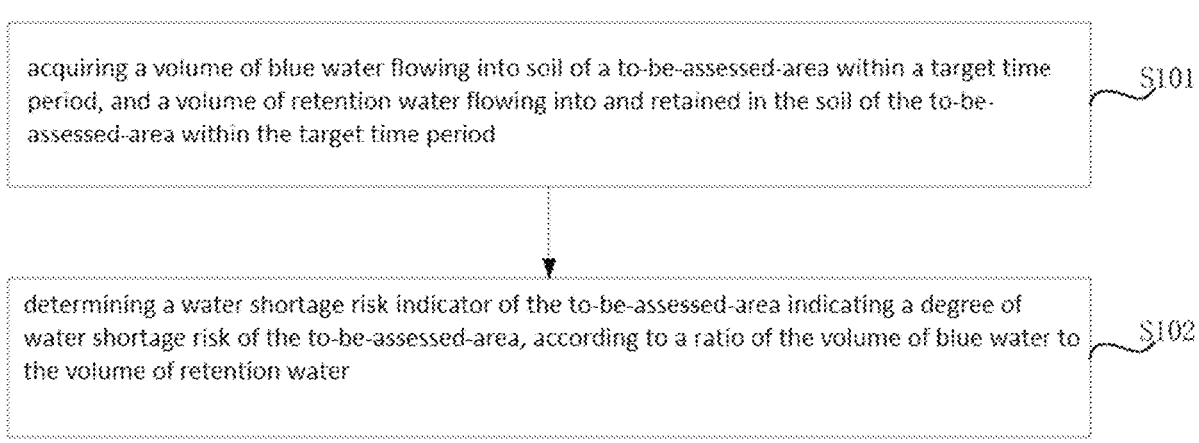
FIG. 2 is a flowchart of a method for assessing water shortage risk provided in an embodiment.

FIG. 2 is a flowchart of a method for assessing water shortage risk provided in an embodiment. The method is conducted by the computer device in FIG. 1, and involves the specific process of determining a water shortage risk indicator of the to-be-assessed-area according to a ratio of the volume of blue water to the volume of retention water by a computer device, and as shown in FIG. 2, the method comprises the following steps:

S101, acquiring a volume of blue water flowing into soil of a to-be-assessed-area within a target time period, and a volume of retention water flowing into and retained in the soil of the to-be-assessed-area within the target time period;

The water resource may comprise blue water resource and green water resource, the blue water resource may refer to the flowing water in rivers, lakes and underground aquifers, the green water resource may refer to the water that flows into the soil through precipitation, such as rainfall, snowfall, etc. Among them, the volume of blue water flowing into the soil of a to-be-assessed-area may refer to the volume of blue water that flows into the soil in the form of irrigation, channel leakage and capillary water. The volume of blue water can indicate the volume of blue water available to the soil in the to-be-assessed-area.

The target time period refers to the time interval for measuring the water shortage risk indicator, and may be determined flexibly according to the assessment demand, for example, when the water shortage risk indicator needs to be evaluated in the last 10 years, the target time period is the last 10 years.

The volume of retention water refers to the amount of water that flows into the soil and is stored in the soil during a target time period. Since the water that flows into and is stored in the soil is consumed in the form of vegetation transpiration or surface evaporation, the amount of water that flows into and is stored in the soil may be taken as the total volume of water that can be used by the soil, that is, the volume of retention water may indicate the total volume of water available to the soil.

S102, determining a water shortage risk indicator of the to-be-assessed-area indicating a degree of water shortage risk of the to-be-assessed-area, according to a ratio of the volume of blue water to the volume of retention water.

Wherein, the ratio of the volume of blue water to the volume of retention water can indicate the demand level of soil for blue water, the higher the ratio, the greater the demand of the soil for the volume of blue water, the soil needs to rely on supplementation of a large amount of blue water to meet its water use demand, that is, the lower the soil's own green water meets the demand for use, the greater the soil's risk of water shortage; and the lower the ratio, the smaller the soil's demand for the volume of blue water, the better the soil's own green water can meets its demand for use, the lower the degree of the water shortage risk of the soil. Therefore, the present application may consider the assessment of the water shortage risk faced by the soil from the perspective of the degree to which the soil's own green water can meet its requirements for use using the ratio of the volume of blue water to the volume of retention water, allowing the determined water shortage risk indicator to more fully represent the degree of water shortage risk of the soil.

The ecological environment, which takes natural objects as elements, is dominated by the environment formed by natural forces rather than humans. Water in the ecological environment is mainly consumed by: prokaryotes, protozoa, fungi, vegetation and animals. With vast distribution and tremendous amount, vegetation consums water that accounts a major share of the total water consumption by the ecological environment. Compared with the water consumption of vegetation, the water consumption of animals and microorganisms is negligible, so the total volume of water used by soil, i.e., the volume of retention water may characterize the water consumption of the ecological environment. And the water shortage risk indicator of to-be-assessed-area determined according to the ratio of the volume of blue water to the volume of retention water may characterize the degree of water shortage risk in the ecological environment.

The water shortage risk indicator is used to indicate the degree of water shortage risk in the to-be-assessed-area. Optionally, the water shortage risk indicator may be denoted in a numerical form, for example, from 1-10, among which a water shortage risk indicator of 10 represents an ultra-high risk of water shortage; a water shortage risk indicator of 9 represents an extremely high risk of water shortage; a water shortage risk indicator of 8 represents a relatively high risk of water shortage; a water shortage risk indicator of 7 represents a high risk of water shortage; and a water shortage risk indicator of 2 represents a low risk of water shortage.

Alternatively, the water shortage risk indicator may optionally be directly characterized by the degree of risk. The degree of risk comprises but is not limited to low risk, medium risk, high risk, and extremely high risk. For example, the water shortage risk indicator indicates a low risk, or a medium risk.

In this embodiment, the specific process of determining the water shortage risk indicator of a to-be-assessed-area according to the ratio of the volume of blue water to the volume of retention water may be: for example, the ratio of the volume of blue water to the volume of retention water is 0.4, the to-be-assessed-area is assigned a weight coefficient according to underlying surface information thereof, for example, if the weight coefficient is 5, thus, the specific method for calculating the water shortage risk indicator of the to-be-assessed-area is: 0.4×5, that is, the water shortage risk indicator of the to-be-assessed-area is 2, and the indicator 2, for example, may represent a low risk of water shortage of the to-be-assessed-area.

In the above embodiment, the water shortage risk indicator of the to-be-assessed-area is determined according to a ratio of the volume of blue water flowing into soil of a to-be-assessed-area to the volume of retention water flowing into and retained in the soil of the to-be-assessed-area, as the volume of blue water can indicate the volume of blue water available to soil in the to-be-assessed-area, and the volume of retention water can indicate the total volume of water available to soil in the to-be-assessed-area, the ratio of the volume of blue water to the volume of retention water can indicate the demand level of soil for blue water. The higher the ratio, the greater the soil's demand for the volume of blue water, that is, the soil's own green water cannot meet the soil's water demand, the soil has the risk of water shortage, has a high dependence on blue water and a relatively high degree of water shortage risk. Therefore, when determining the water shortage risk indicator of the to-be-assessed-area, in the present application, the volume of blue water demanded by the soil is taken into account, so that the determined water shortage risk indicator can indicate the degree of water shortage risk of the ecological environment, and improves comprehensiveness compared with methods in the related technology to determine whether there is a risk of water shortage in a region according to the relationship between the amount of water that can be provided to human production activities and the water demand for human activities in the region.

The above determination of the water shortage risk indicator of a to-be-assessed-area according to a ratio of the volume of blue water to the volume of retention water may be implemented in many ways, and optionally, may include: matching the ratio of the volume of blue water to the volume of retention water with a first mapping relation, which comprises corresponding relation of different ratio ranges with the water shortage risk indicator, to determine the water shortage risk indicator in the to-be-assessed-area.

Wherein, the first mapping relation may be pre-set according to assessment requirements, and is used to indicate the corresponding relation between the ratio of the volume of blue water to the volume of retention water with the water shortage risk indicator. For example, the first mapping relation may be shown in Table 1:

TABLE 1

| water shortage risk indicator | ratio range of volume of blue water to volume of retention water |
| --- | --- |
| 1 | [0, 0.25) |
| 2 | [0.25, 0.5) |
| 3 | [0.5, 0.75) |
| 4 | [0.75, 1) |

For example, assuming that the ratio of the volume of blue water to the volume of retention water is 0.8, which falls into the ratio range of [0.75, 1), according to the first mapping relation in Table 1, it can be seen that a water shortage risk indicator 4 corresponds to the ratio range, wherein a water shortage risk indicator of 4 may represent an extremely high risk of water shortage, that is, the water shortage risk of the ecological environment of the area is extremely high.

Alternatively, in this embodiment, the first mapping relation may be shown as Table 2:

TABLE 2

| water shortage risk indicator | ratio range of volume of blue water to volume of retention water |
|---|---|
| low risk | [0, 0.25) |
| medium risk | [0.25, 0.5) |
| high risk | [0.5, 0.75) |

In this embodiment, assuming that the ratio of the volume of blue water to the volume of retention water is 0.3, which falls into the ratio range of [0.25, 0.5), according to the first mapping relation in Table 2, it can be seen that, the water shortage risk indicator corresponding to the ratio range is medium risk.

Alternatively, determining the water shortage risk indicator of the natural system in the to-be-assessed-area according to the ratio of the volume of blue water to the volume of retention water may specifically include: taking the ratio of the volume of blue water to the volume of retention water as the water shortage risk indicator of the to-be-assessed-area.

For example, the ratio of the volume of blue water to the volume of retention water is 0.2, thus, the water shortage risk indicator of to-be-assessed-area is 0.2. Each value of the water shortage risk indicator has a corresponding degree of risk, e.g., a water shortage risk indicator of 0.2 for the to-be-assessed-area represents that the water shortage risk in the area is low.

It should be noted that, in this embodiment, since the ratio of the volume of blue water to the volume of retention water is less than 1 and greater than 0, the range of the corresponding water shortage risk indicator is also less than 1 and greater than 0, and may be shown as Table 3. The range of 0-1 may be divided to form multiple ranges of the indicator, which correspond to the degree of risk, for example, the ratio of the amount of blue water to the volume of retention water is 0.6, thus, the water shortage risk indicator of to-be-assessed-area is 0.6, falling into the indicator range of [0.5, 0.75), thus, the water shortage risk of to-be-assessed-area is high.

TABLE 3

| degree of risk | range of water shortage risk indicator |
|---|---|
| low risk | [0, 0.25) |
| medium risk | [0.25, 0.5) |
| high risk | [0.5, 0.75) |
| extremly high risk | [0.75, 1) |

Optionally, the water shortage risk indicator may indicate the degree of the water shortage risk in the ecological environment of the-be-assessed-area; or, optionally, the water shortage risk indicator may indicate the degree of the water shortage risk of the ecological environment and human society in the to-be-assessed-area.

Figure 3:
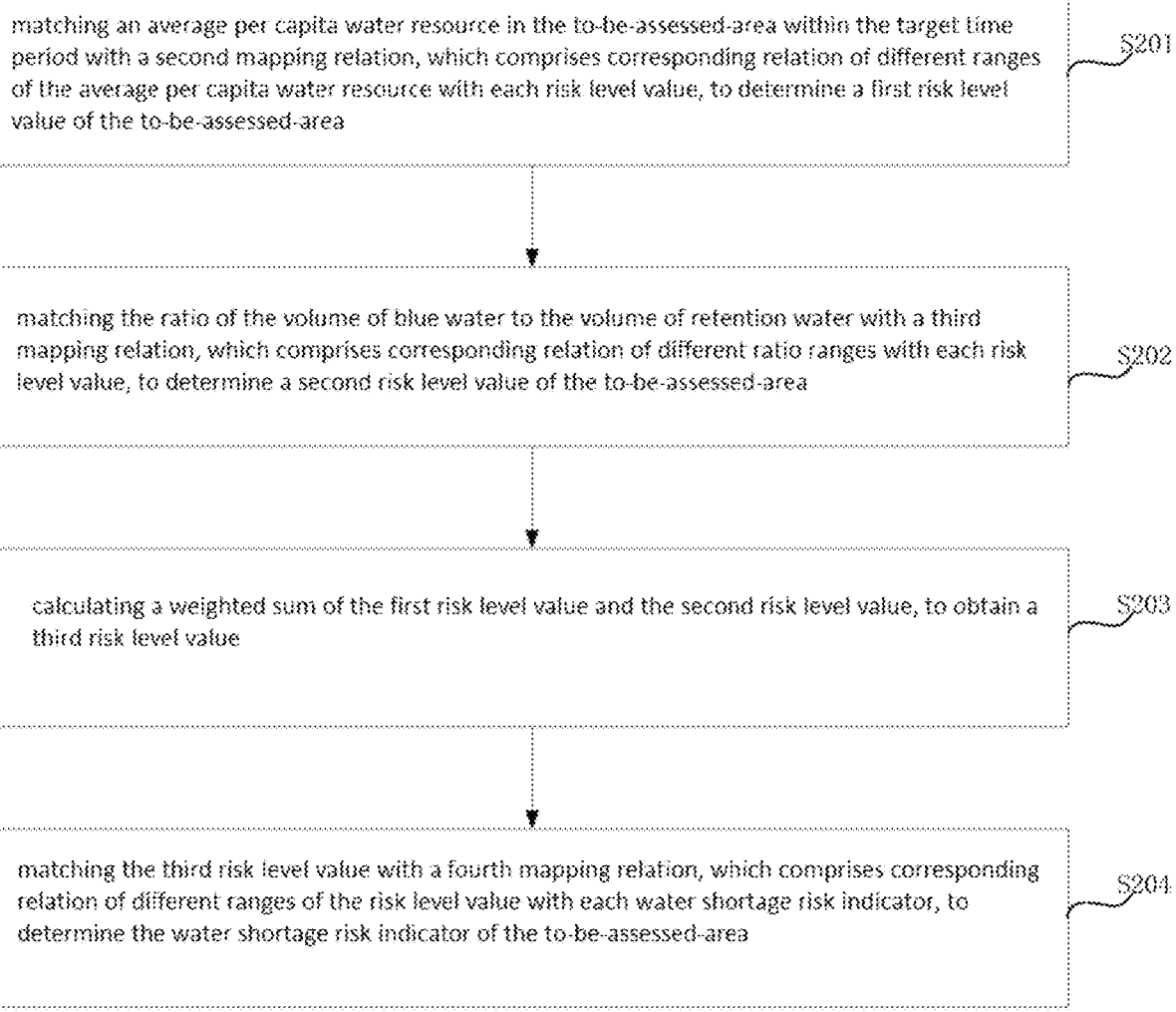
FIG. 3 is a flowchart of a method for assessing water shortage risk provided in another embodiment.

As shown in FIG. 3, which is a flowchart of a method for assessing water shortage risk provided in another embodiment. The method is executed by the computer device in FIG. 1, and involves the specific process of determining the water shortage risk indicator that may determine the degree of water shortage risk in the ecological environment while indicating the degree of water shortage risk in human society by the computer device, the method includes the following steps:

S201, matching an average per capita water resource in the to-be-assessed-area within the target time period with a second mapping relation, which comprises corresponding relation of different ranges of the average per capita water resource with each risk level value, to determine a first risk level value of the to-be-assessed-area, the second mapping relation;

Wherein, the first risk level value is used to indicate the degree of water shortage risk of water that can be provided to human activities, and is determined by the average per capita water resource and the second mapping relation. The water resource that can be used for human activities is blue water resource.

In this embodiment, assuming that the target time period is the last 1 year, and the population and the available total volume of blue water resource in the to-be-assessed-area in the last 1 year can be obtained by any optional means such as measurement, statistics, or data simulation.

For example, the population in the year of 2018 is 20, and the total volume of available blue water resource is 30,000 cubic meters per year. Thus, the average per capita water resource in 2018 is 1500 cubic meters per year.

The second mapping relation is for example, shown as Table 4:

TABLE 4

| value of risk level | range of average per capita water resource (unit: cubic meters per person per year) |
|---|---|
| 1 | [1700, 10000) |
| 2 | [1000, 1700) |
| 3 | [500, 1000) |
| 4 | [0, 500) |

The second mapping relation comprises different ranges of average per capita water resource and different risk level values.

In 2018, the average per capita water resource is 1500 cubic meters per year, less than 1700 cubic meters per year, and greater than or equal to 1000 cubic meters per year, the corresponding first risk level value is 2.

It should be noted that, different risk level values in the second mapping relation correspond to different risk levels, for example, a risk level value of 1 indicates that the amount of water resource basically meets requriements for local social development, and the risk level is defined as low risk; a risk level value of 2 indicates that the area will experience periodic or regular water stress, the risk level is defined as medium risk; a risk level value of 3 indicates that the area will experience continuous water shortage and loss in economic development and people's health being undermined, and the risk level is defined as high risk; a risk level value of 4 indicates that the area will experience extremely severe water shortage, which will seriously affect the social and economic development and people's health, and the risk level is defined as extremely high risk.

S202, matching the ratio of the volume of blue water to the volume of retention water with a third mapping relation, which comprises corresponding relation of different ratio ranges with each risk level value, to determine a second risk level value of the to-be-assessed-area.

Among them, the second risk level value is used to indicate the degree of water shortage risk for water source that can be provided to the ecological environment, and is determined by the ratio of the volume of blue water and the volume of retention water and the third mapping relation. The water resource that can be provided to the ecological environment comprises green water and part of the blue water supplied to the soil. The greater the ratio of the volume of blue water to the volume of retention water, the greater the ecological environment's demand for blue water, that is, the lower the degree to which green water of the to-be-assessed-area can meet the soil's demand for water, and the greater the risk of water shortage of the soil in the to-be-assessed-area.

In this embodiment, for example, the target time period is the last 1 year, and the ratio of the volume of blue water to the volume of retention water in the to-be-assessed-area in the last 1 year is obtained by any optional means such as measurement, statistics, or data simulation, for example, the ratio of the volume of blue water to the volume of retention water in 2018 is 0.1.

The third mapping relation is shown as Table 5:

TABLE 5

| risk level value | ratio range of volume of blue water to volume of retention water |
|---|---|
| 1 | [0, 0.25) |
| 2 | [0.25, 0.5) |
| 3 | [0.5, 0.75) |
| 4 | [0.75, 1) |

The third mapping relation comprises different ranges of the ratio of the volume of blue water to the volume of retention water and different risk level values.

In 2018, the ratio of the volume of blue water to the volume of retention water is 0.1, falling into the range of [0, 0.25), corresponding to a second risk level value of 1.

It should be noted that, in this embodiment, a risk level value of 1 indicates that water consumed by the soil mainly depends on the green water resource, and does not depend on the blue water resource, and the potential risk level of water resource shortage is low. A risk level value of 2 indicates that water consumed by the soil depends on the green water resource and part of the blue water resource, the potential risk level of water resource shortage is medium; a risk level value of 3 indicates that water consumed by the soil is more dependent on blue water resource, the potential risk level of water resource shortage is high; a risk level value of 4 indicates that water consumed by the soil is excessively dependent on blue water resource, and the potential risk level of water resource shortage is extremely high.

S203, calculating a weighted sum of the first risk level value and the second risk level value, to obtain a third risk level value.

Specifically, for example, in 2018, the water shortage risk weight of human society is 0.4, and the water shortage risk weight of the ecological environment is 0.6.

The first risk level value and the second risk level value are weighted and summed, specifically as shown in Formula 1:

$$R = \left( \sum_{i=1}^{N} R_h \times W_h + R_e \times W_e \right) / n \qquad \text{Formula 1}$$

Wherein $R_h$ is the first risk level value (equal to 1, 2, 3, 4), $W_h$ is the water shortage risk weight of human society, $R_e$ is second risk level value (equal to 1, 2, 3, 4), $W_e$ is the water shortage risk weight $W_e = 1 - W_h$ of the ecological environment, and n is the target time period, in this embodiment, the target time period n=1.

Thus, in combination with the Formula 1 and the first risk level value in 2018, the second risk level value is calculated as:

$$R = \frac{2 \times 0.4 + 1 \times 0.6}{1} = 1.4,$$

and the third risk level value obtained is 1.4.

S204, matching the third risk level value with a fourth mapping relation, and determining the water shortage risk indicator of the to-be-assessed-area, the fourth mapping relation comprises corresponding relation of different ranges of the risk level value with each water shortage risk indicator.

The fourth mapping relation may be flexibly set according to the assessment needs, and includes different risk level value ranges and different water shortage risk indicator, as shown in Table 6:

TABLE 6

| water shortage risk indicator | range of risk level value |
|---|---|
| 1 | 0 ≤ R < 2 |
| 2 | 2 ≤ R < 4 |
| 3 | 4 ≤ R < 6 |
| 4 | 6 ≤ R < 8 |

The third risk level value is 1.4, it can be seen according to the fourth mapping relation that, the water shortage risk indicator of to-be-assessed-area is 1, and each risk indicator corresponds to a different risk level, e.g., a water shortage risk indicator of 1 represents a low risk.

Alternatively, in this embodiment, the fourth mapping relation may further be shown as Table 7:

TABLE 7

| water shortage risk indicator | range of risk level value |
|---|---|
| low risk | 0 ≤ R < 2 |
| medium risk | 2 ≤ R < 4 |
| high risk | 4 ≤ R < 6 |
| extremely high risk | 6 ≤ R < 8 |

When the third risk level value is 1.4, it can be seen from the fourth mapping relation in Table 7 that the water shortage risk indicator of the to-be-assessed-area is low.

Alternatively, in this embodiment, the water shortage risk indicator of the to-be-assessed-area may be determined according to the third risk level value, specifically, the third risk level value may be taken as the water shortage risk indicator of the to-be-assessed-area.

For example, if the third risk level value is 1.4, thus, the water shortage risk indicator of the to-be-assessed-area is 1.4. The value of the water shortage risk indicator corresponds to a certain risk level, for example, the water shortage risk indicator of the to-be-assessed-area being 1.4 represents that the water shortage risk of the area is low.

Alternatively, in this embodiment, the water shortage risk indicator of the to-be-assessed-area may be determined according to the third risk level value, and specifically, If the third risk level value is 1.4, the to-be-assessed-area is endowed with a weight coefficient according to underlying surface information of the to-be-assessed-area, for example, if the weight coefficient is 0.8, thus, the water shortage risk indicator of the to-be-assessed-area is specifically calculated as 1.4×0.8=1.12, i.e., the water shortage risk indicator of the to-be-assessed-area is 1.12, indicating a low water shortage risk of the to-be-assessed-area.

On the basis of the above-mentioned embodiment, this implementation also provides a method for determining the water shortage risk indicator, for example: assuming that the target time period is 5 years, the population in each of the 5 years and the total volume of the available blue water resource in each of the 5 years in the to-be-assessed-area are obtained via measurement, statistics or data simulation and other optional methods. Assuming that the target time period stretches from 2001 to 2005, and the population in 2001 is 20, the total volume of the available blue water resource is 30,000 cubic meters per year; in 2002, the population is 20, the total volume of the available blue water resource is 40,000 cubic meters per year; the population in 2003 is 24, the total volume of the available blue water resource is 20,000 cubic meters per year; in 2004, the population is 26, the total volume of the available blue water resource is 10,000 cubic meters per year; the population in 2005 was 26, the total volume of the available blue water resource is 20,000 cubic meters per year.

Correspondingly, the average per capita water resource in 2001 is 30000/20=1500 cubic meters per year; the average per capita water resource in 2002 is 40000/20=2000 cubic meters per year; the average per capita water resource in 2003 is: 20000/24=833.33 cubic meters per year; the average per capita water resource in 2004 is: 10000/26=384.62 cubic meters per year; the average per capita water resource in 2005 is: 20000/26=769.23 cubic meters per year.

In the present application, the first risk level value of each year is calculated according to the average per capita water resource of each year, and referring to the second mapping relation shown in Table 4, it may be sees that in 2001, the average per capita water resource is 1500 cubic meters per year, less than 1700 cubic meters per year and greater than or equal to 1000 cubic meters per year, the corresponding first risk level value is 2. Likewise, the corresponding first risk level value in 2002 is 1, the corresponding first risk level value in 2003 is 3, and the corresponding first risk level value in 2004 is 4, and the corresponding first risk level value in 2005 is 3.

The ratio of the volume of blue water to the volume of retention water in the to-be-assessed-area in 2001-2005 is obtained by any optional method such as measurement, statistics or data simulation, for example, the ratio of the volume of blue water to the volume of retention water in 2001 is 0.1; the ratio of the volume of blue water to the volume of retention water in 2002 is 0.6; the ratio of the volume of blue water to the volume of retention water in 2003 is 0.8; the ratio of the volume of blue water to the volume of retention water in 2004 is 0.3; and the ratio of the volume of blue water to the volume of retention water in 2005 is 0.2.

Referring to the third mapping relation shown in Table 5, it may be seen that in 2001, the ratio of the volume of blue water to the volume of retention water is 0.1, greater than or equal to 0 and less than 0.25, and the corresponding second risk level value is 1. Meanwhile, the corresponding second risk level value in 2002 is 3, the corresponding second risk level value in 2003 is 4, the corresponding second risk level value in 2004 is 2, and the corresponding second risk level value in 2005 is 1.

It should be noted that, the second mapping relation has the same number of risk level values as the third mapping relation in the present application, that is, the corresponding risk level value in the second mapping relation has 4 values, the corresponding risk level in the third mapping relation also has 4 values. Thus, division of levels of the water shortage risk for water provided to the ecological environment is compatible with that of the water shortage risk for water provided for human activities.

The water shortage risk weight for the human society and the water shortage risk weight for the ecological environment each year are obtained, for example shown as Table 8:

TABLE 8

| 2001-2005 | water shortage risk weight for human society | water shortage risk weight for ecological environment |
|---|---|---|
| 2001 | 0.5 | 0.5 |
| 2002 | 0.4 | 0.6 |
| 2003 | 0.6 | 0.4 |
| 2004 | 0.7 | 0.3 |
| 2005 | 0.6 | 0.4 |

Thus, in combination with the Formula 1 and the corresponding first risk level values in 2001-2005, the second risk level value is calculated as follows:

$$R = \frac{(2\times0.5 + 1\times0.5) + (1\times0.4 + 3\times0.6) + (3\times0.6 + 4\times0.4) + (4\times0.7 + 2\times0.3) + (3\times0.6 + 1\times0.4)}{5} = 2.54$$

The obtained third risk level value is 2.54. Referring to the fourth mapping relation shown as Table 6, it can be seen that the third risk level value is 2.54, the water shortage risk indicator of the to-be-assessed-area is 2, indicating a medium risk. That is, within the target time period of 5 years, the water shortage risk of to-be-assessed-area is medium.

In the above embodiment, the first risk level value is determined according to average per capita water resource and the second mapping relation, and the second risk level value is determined according to the ratio of the volume of the blue water to the volume of retention water and the third mapping relation, the first risk level value and the second risk level value are weighted and summed to obtain the third risk level value, and the water shortage risk indicator of the to-be-assessed-area is determined according to the third risk level value. As the first risk level can indicate the water shortage risk for the human society, and the second risk level value can indicate the water shortage risk for the ecological environment, the third risk level value obtained by weighting and summation of the first risk level value and the second risk level value embody both the water shortage risk for the human society and the water shortage risk for the soil, and can comprehensively indicate the water shortage risk of the to-be-assessed-area, thus the water shortage risk indicator of the to-be-assessed-area determined according to the third risk level value can more comprehensively indicate the degree of the water shortage risk for the to-be-assessed-area, resulting into a more comprehensive assessment result.

Figure 4:
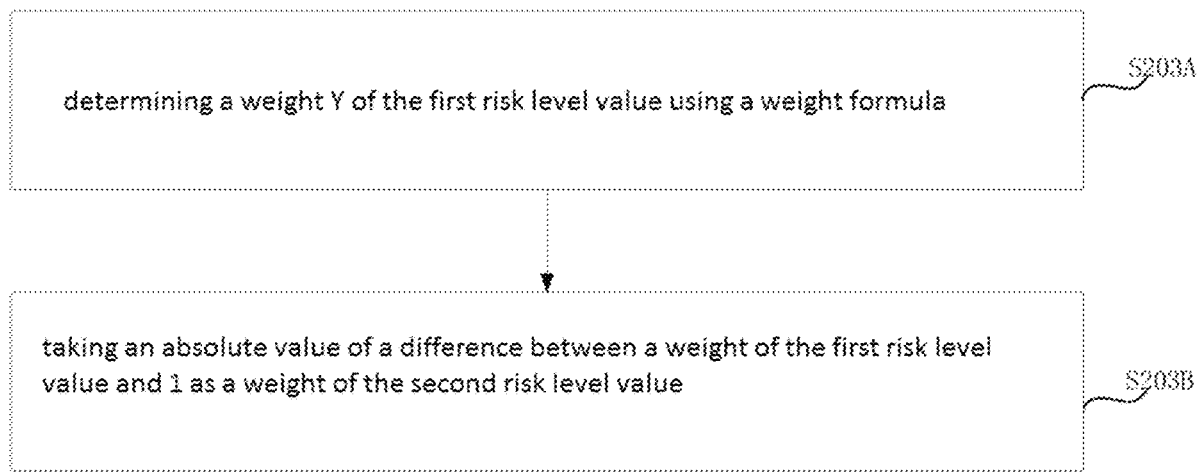
FIG. 4 is a flowchart of a method for assessing water shortage risk which provided in a further embodiment.

In the above weighted summation process, the water shortage risk weight for the human society indicates the degree of impact of water consumed by the human society on the ecological environment, and the water shortage risk weight for the ecological environment indicates the degree of impact of water consumed by the ecological environment on the ecological environment, it is very important to determine the water shortage risk weight for the human society and the water shortage risk weight for the ecological environment scientifically and reasonably. And as shown in FIG. 4, in this embodiment, before the first risk level value and the second risk level value are subjected to weighted summation to obtain the third risk level value, the method also comprises:

S203A, determining a weight Y of the first risk level value using a weight formula.

Wherein the weight formula is $Y=aX+b$, wherein X represents a total volume of blue water resource in the to-be-assessed-area, a represents slope, b represents intercept; wherein the slope a and the intercept b may be given a value according to experience, or calculated according to curve fitting technique, in this embodiment, the curve fitting technique is taken as an example to make the description:

Firstly, a linear regression curve is established as $y=ax+b$, according to the curve fitting technique.

Secondly, the total volume X of the blue water resource in the to-be-assessed-area and the human society blue water consumption C are obtained by any method such as measurement, statistics or data simulation, and the proportion of water resource consumed by the human society $y1=C/X$ is obtained according to the total volume X of the blue water resource in the to-be-assessed-area and the human society blue water consumption C.

According to the above method, (y1, X1)(y2, X2) of multiple target time periods for the to-be-assessed-area is obtained; and (y1,X1)(y2,X2) is substituted in the fitting curve $y=ax+b$, to calculate the slope a and the intercept b.

For example, the calculated slope $a=-0.1$, and intercept $b=0.8$, thus, the weight formula for the first risk level value is $Y=-0.1X+0.8$. For example, the blue water resource total volume in 2001 is 30000 cubic meters per year, thus, the corresponding first risk level value weight in 2001 is $-0.1 \times 3+0.8=0.5$.

S203B, taking an absolute value of a difference between a weight of the first risk level value and 1 as a weight of the second risk level value.

In an ideal environment, it is generally believed that the blue water resource are completely consumed by the human society and the soil. Therefore, the sum of the weight of the first risk indicator weight and the second risk indicator weight should be 1. In this embodiment, 2001 is still used as an example for explanation, the first risk level value weight for 2001 is 0.5, thus, the water shortage risk weight for the ecological environment is $1-0.5=0.5$.

In the above embodiment, the weight of the first risk level value and the weight of the second risk level value are obtained through reasonable calculation, so that the third risk level value obtained by weighted summation can better indicate the water shortage risk of the to-be-assessed-area. Therefore, the water shortage risk indicator determined according to the third risk level value is also more accurate.

Since the water in the soil has multiple inflow and outflow paths, when acquiring the volume of blue water and the volume of retention water, it is necessary to comprehensively and accurately obtain the multiple inflow paths of water and the corresponding amount of water for each inflow path, and the multiple outflow paths of water and the corresponding amount of water for each outflow path, so as to accurately obtain the volume of blue water and the volume of retention water, and thus, obtain an accurate water shortage risk indicator. Based on this, as shown in FIG. 5, in this embodiment, the volume of blue water flowing into the to-be-assessed-area soil within a target time period, and the volume of retention water flowing into and retained in the to-be-assessed-area soil within the target time period are obtained in the form of hydrological simulation, the specific process is as follows:

S301, the ecological hydrological simulation is carried out through an ecological hydrological model to obtain the simulation result, including the volume of blue water, the volume of outflow water which flows out from the soil of the to-be-assessed-area within the target time period, and the volume of vegetation retention water.

Water resource in the soil is consumed in the form of evapotranspiration, which mainly consumes water in soil, including green water resource formed by precipitation and replenishment to the soil caused by other factors, such as irrigation caused by human activities and channel leakage caused by irrigation channels, capillary water caused by natural factors, etc. Due to the different water resources, the soil consumes both the green water resource and the blue water resource. In this embodiment, simulation is carried out according to the ecological hydrological model, wherein water flowing into and out of the soil is classified. Specifically, the simulation result of the ecological hydrological simulation conducted via the ecological hydrological model includes the volume of blue water, the volume of outflow water, the volume of vegetation retention water, wherein the volume of blue water includes the volume of irrigation water Ir caused by human activities and volume of channel leakage SP leakage caused by irrigation channels, and the volume of capillary water CP caused by natural factors, specifically, the volume of blue water=the volume of irrigation water Ir+the volume of channel leakage SP+the volume of capillary water CP.

The volume of outflow water comprises a volume of surface runoff water RH, a volume of groundwater supplied Re and a volume of subsurface flow IF, wherein, the volume of surface runoff water RH is the amount of water generated on the ground and flowing into a certain water-carrying cross-section along the ground, the volume of groundwater supplied Re is the amount of water supplemented from the soil to the groundwater layer; the volume of subsurface flow IF refers to water flow that flows laterally in the upper soil layer or on the interface of layered soil layers.

The volume of the green water resource formed by precipitation may be calculated through the precipitation P and the volume of vegetation retention water Int. Specifically, during rainfall or snowfall, due to vegetation retention, some precipitation will be retained in the vegetation canopy, and then directly evaporated as water vapor to enter the atmosphere and does not flow into the soil. Only the precipitation that flows into the soil can form the green water resource, that is, effective prescription Pe, wherein $Pe=P-Int$, P represents the precipitation in the to-be-assessed-area within a target time period, Int represents the vegetation retention water Int in the to-be-assessed-area.

Int represents the maximum retention capacity of vegetation canopy in the to-be-assessed-area, $Int=0.3 \times LAI$, LAI is a leaf area index and can be is obtained through the Global Leaf Area Index database (http://glcf.umd.edu/data/lai/) or Remote sensing inversion real-time database (https://neo.sci.gsfc.nasa.gov/view/php?dataseId=MOD15A2_M_LAI).

S302, obtaining the volume of retention water according to precipitation, the volume of vegetation retention water, the volume of blue water and the volume of outflow water within the target time period.

Wherein, the volume of retention water refers to the water flowing into and retained in the soil in the to-be-assessed-area within a target time period, so the volume of retention water is calculated as the difference between all the water flowing into the soil and water flowing out of the soil, that is, the volume of retention water=the volume of irrigation water Ir+the volume of channel leakage SP+the volume of capillary water CP+(precipitation p-vegetation interception Int)−(the volume of surface runoff water RH+the volume of groundwater supplied Re+the volume of subsurface flow IF).

On the basis of the above volume of blue water and volume of retention water, in this embodiment, the ratio of the volume of blue water to the volume of retention water is denoted as BWCR, specifically:

$$BWCR = \frac{Ir + SP + CP}{Ir + SP + CP + (P - Int) - (RH + Re + IF)}$$

In the above embodiment, the hydrological simulation is carried out through the ecological hydrological model, the volume of blue water is determined according to the volume of irrigation water Ir caused by human activity factors and the volume of channel leakage SP caused by irrigation channels, and the volume of capillary water CP caused by natural factors, and the volume of Retention water is determined according to the volume of irrigation water Ir, the volume of channel leakage SP, the volume of capillary water CP, the precipitation p, the volume of vegetation interception Int, the volume of surface runoff water RH, the volume of groundwater supplied Re and the volume of subsurface flow IF, thus both the volume of blue water and the volume of retention water are comprehensively and accurately determined, improving the accuracy of the water shortage risk indicator determined according to the ratio of the volume of blue water to the volume of retention water.

Figure 6:
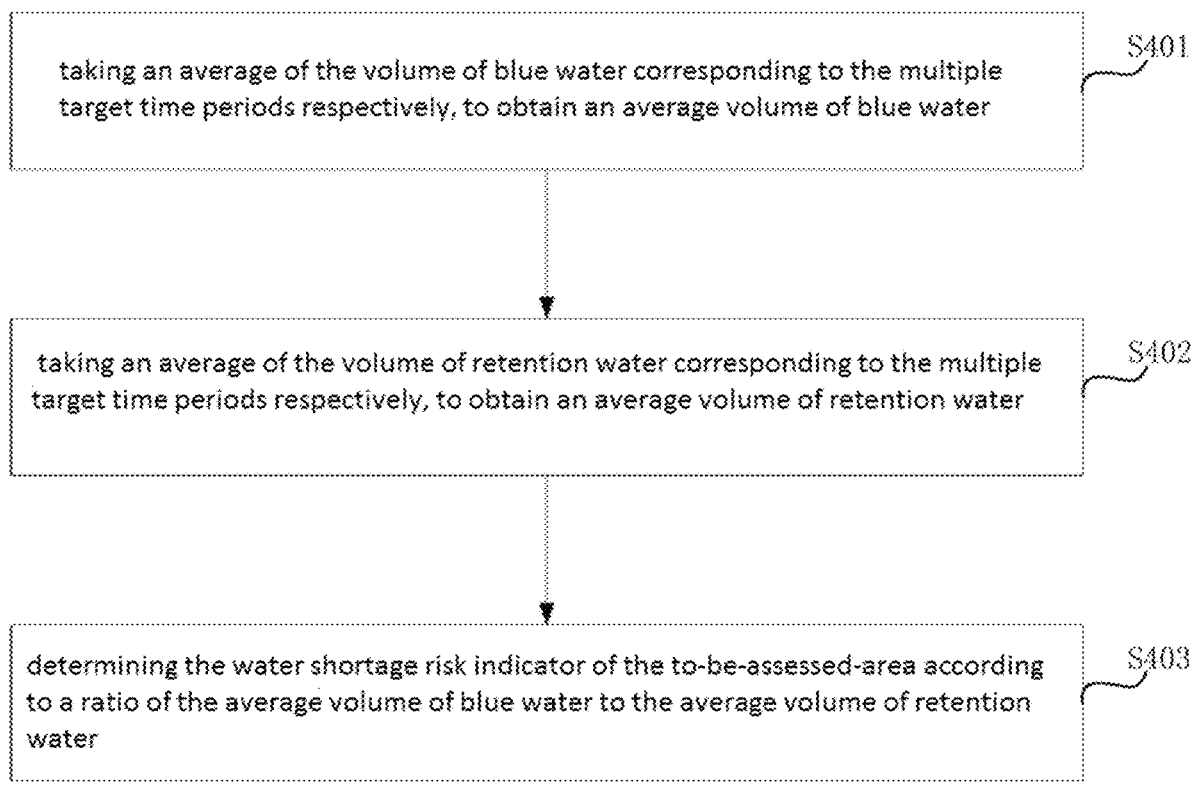
FIG. 6 is a flowchart of a method for assessing water shortage risk which provided in a further embodiment.

Since the volume of blue water and the volume of retention water measured during a target time period are accidental, the accuracy of the water shortage risk indicator determined according to the ratio of the volume of blue water to the volume of retention water within the target time period is less accurate, optionally, in order to solve this problem, the application is carried out in multiple target time periods, as shown in FIG. 6, the method is carried out by the computer device in FIG. 1, and involves specific processes of using the computer device to determine the water shortage risk indicator of the to-be-assessed-area according to the average volume of blue water and average volume of retention water during multiple target time periods, and the method specifically comprises the following steps:

S401, taking an average of the volume of blue water corresponding to the multiple target time periods respectively, to obtain an average volume of blue water.

For example, in this embodiment, 3 target time periods are set, each for 1 year, for example, the volume of blue water is 1200 cubic meters per year in 2010, the volume of blue water is 600 cubic meters per year in 2011; and the volume of blue water is 900 cubic meters per year in 2012. Thus, the average volume of blue water within the 3 target time periods is 900 cubic meters per year.

S402, taking an average of the volume of retention water corresponding to the multiple target time periods respectively, to obtain an average volume of retention water.

In this embodiment, the volume of retention water is respectively: the volume of retention water is 3000 cubic meters per year in 2010; in 2011, the volume of retention water is 3500 cubic meters per year; in 2012, the volume of retention water is 1750 cubic meters per year. Thus, the average volume of retention water within the 3 target time periods is 2750 cubic meters per year.

S403, determining the water shortage risk indicator of the to-be-assessed-area according to a ratio of the average volume of blue water to the average volume of retention water.

The ratio of the volume of blue water to the volume of retention water is denoted as BWCR, BWCR=900/2750=0.32.

The method of determining the water shortage risk indicator of the to-be-assessed-area according to BWCR may select any one of the implementations provided above, for example: according to the mapping relation shown as Table 9, BWCR and the mapping relation, it may be seen that BWCR falls into the rage of [0.25, 0.5), corresponding to a water shortage risk indicator of 2, indicating a medium risk.

TABLE 9

| water shortage risk | ratio ranges of volume of blue water |
|---|---|
| 1 | [0, 0.25) |
| 2 | [0.25, 0.5) |
| 3 | [0.5, 0.75) |
| 4 | [0.75, 1) |

Figure 7:
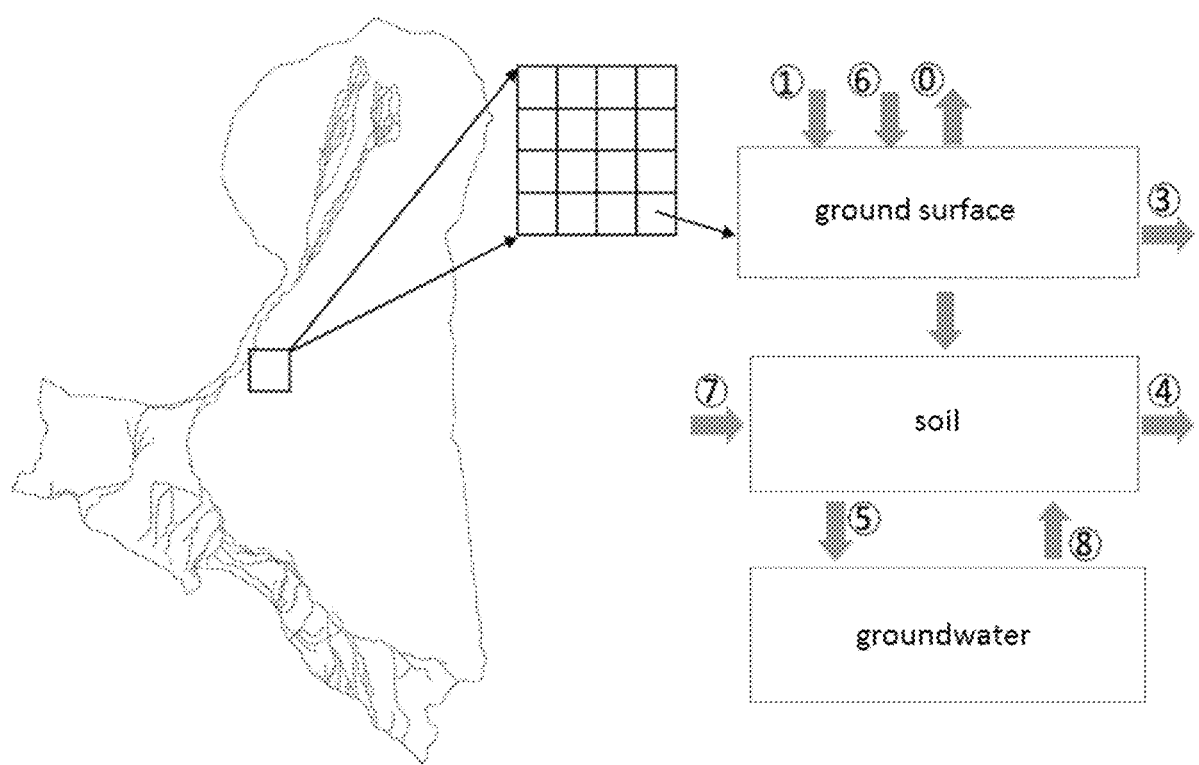
FIG. 7 is a schematic diagram of water flowing into and out of soil in the to-be-assessed-area in the Heihe River Basin.

On the basis of the above-mentioned embodiment, this embodiment will be described with examples:

As shown in FIG. 7, which is a schematic diagram of water flowing into and out of soil in the to-be-assessed-area in the Heihe River Basin. The box marked in the Heihe River Basin is a to-be-assessed-area, which may be divided into multiple small units as shown in the grid in FIG. 7 to facilitate data collection, and data in a small range represented by the each unit are collected before statistic calculation, to obtain collected data of the to-be-assessed-area, on the basis of which ecological hydrological simulation is performed, to obtain the volume of blue water and the volume of retention water. The types of inflow and outflow of water in the soil are further shown in FIG. 7, with arrows toward the soil representing water flowing into the soil, and arrows away from the soil representing water flowing out of the soil. The water flowing into the soil comprises: rainwater, irrigation, capillary water, and channel leakage; and the water flowing out of the soil comprises: ground surface runoff, subsurface flow, and groundwater supply.

Figure 8A:
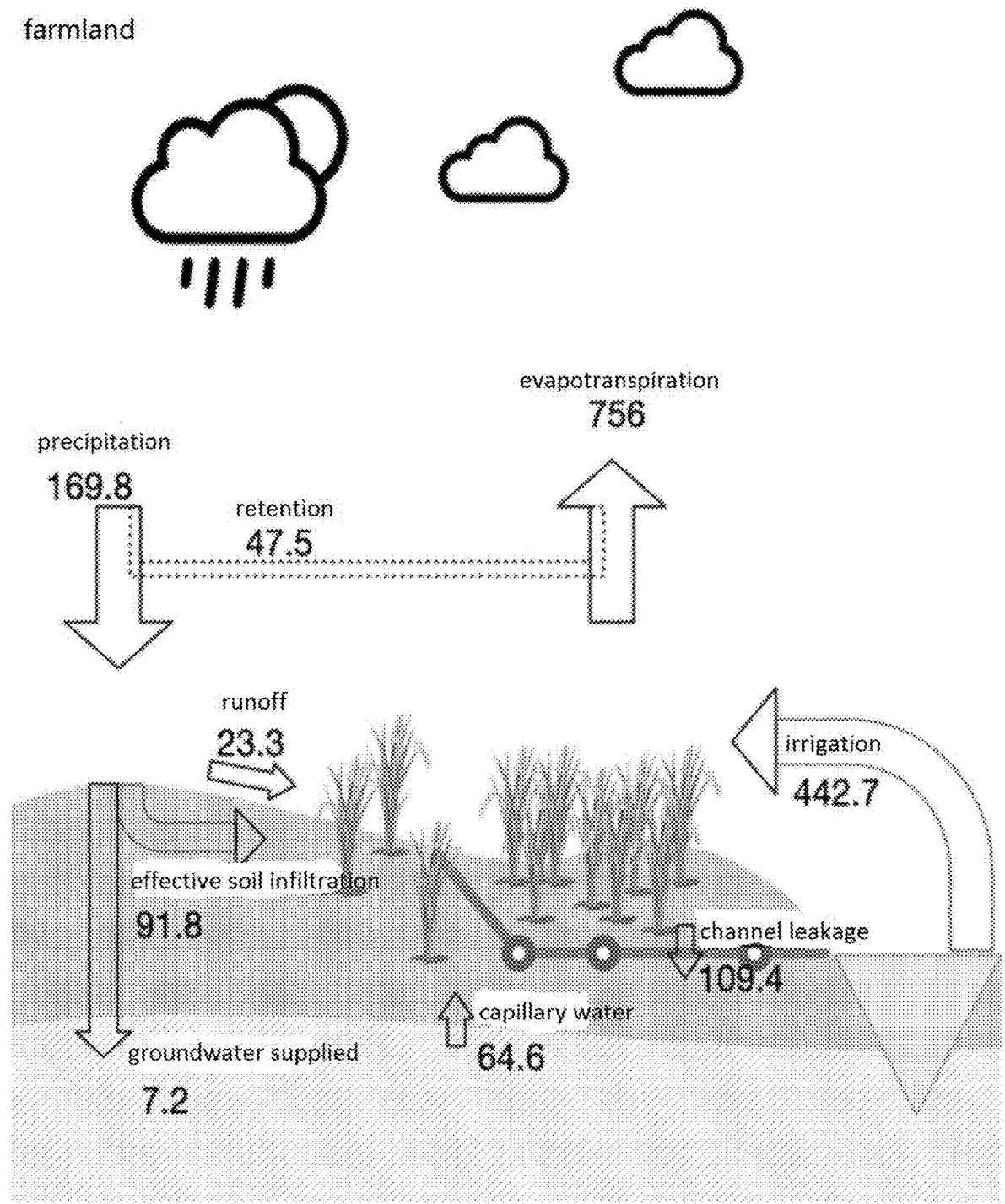
FIG. 8(a) is a schematic diagram of water circulation in soil when the soil type of to-be-assessed-area is farmland.
Figure 8B:
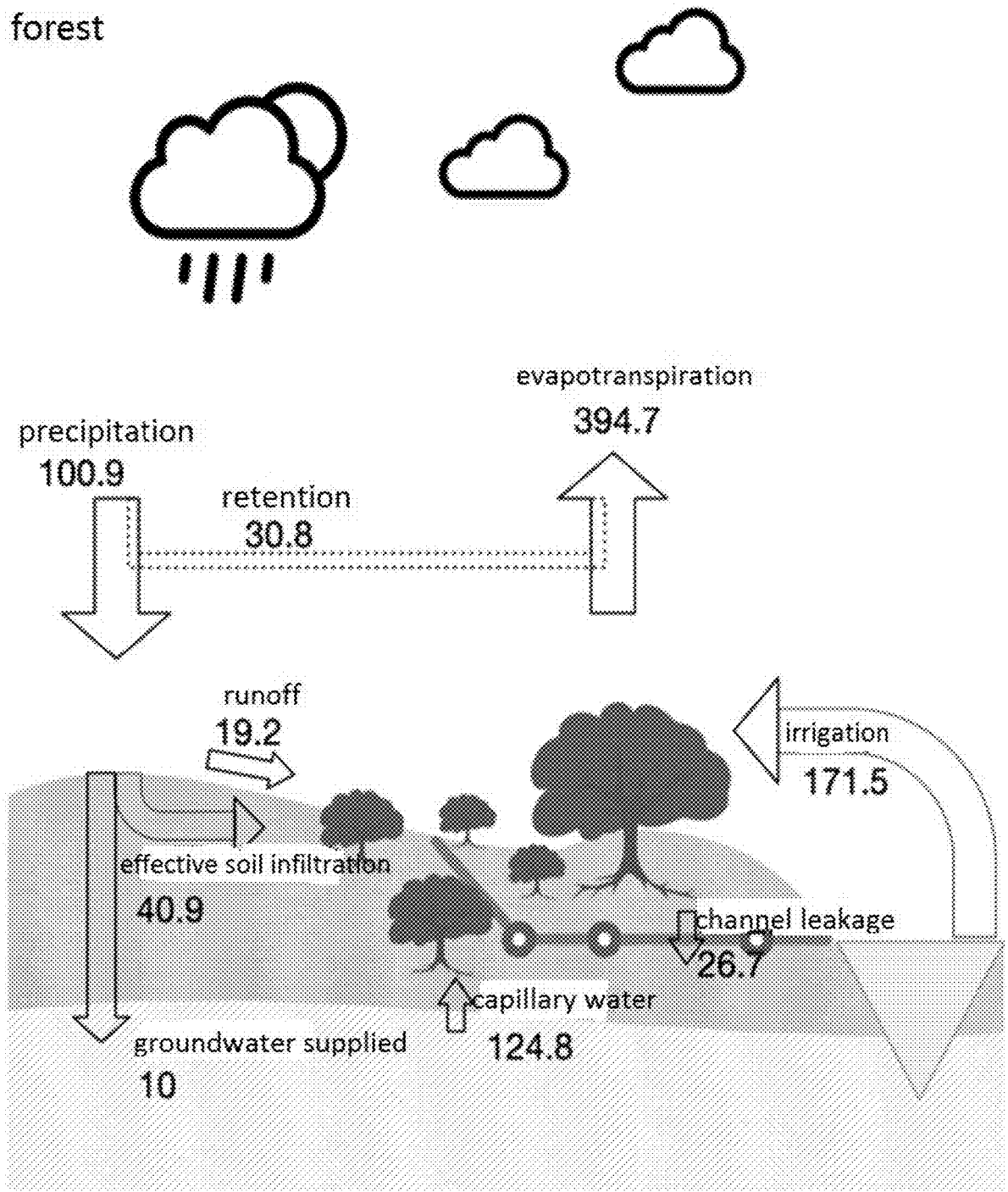
FIG. 8(b) is a schematic diagram of water circulation in soil when the soil type of to-be-assessed-area is forest.
Figure 8C:
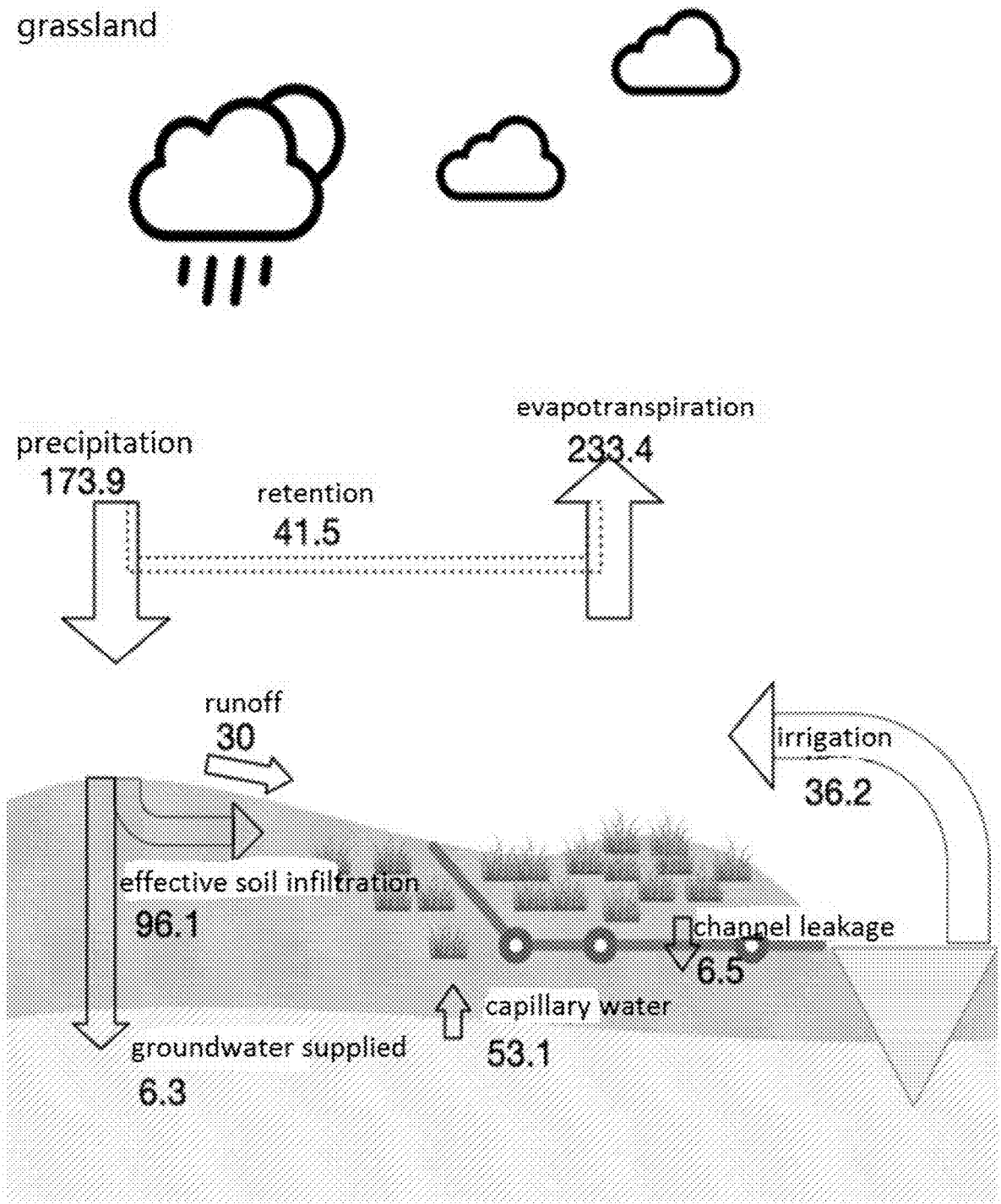
FIG. 8(c) is a schematic diagram of the water circulation in the soil when the soil type of to-be-assessed-area is grassland.
Figure 8D:
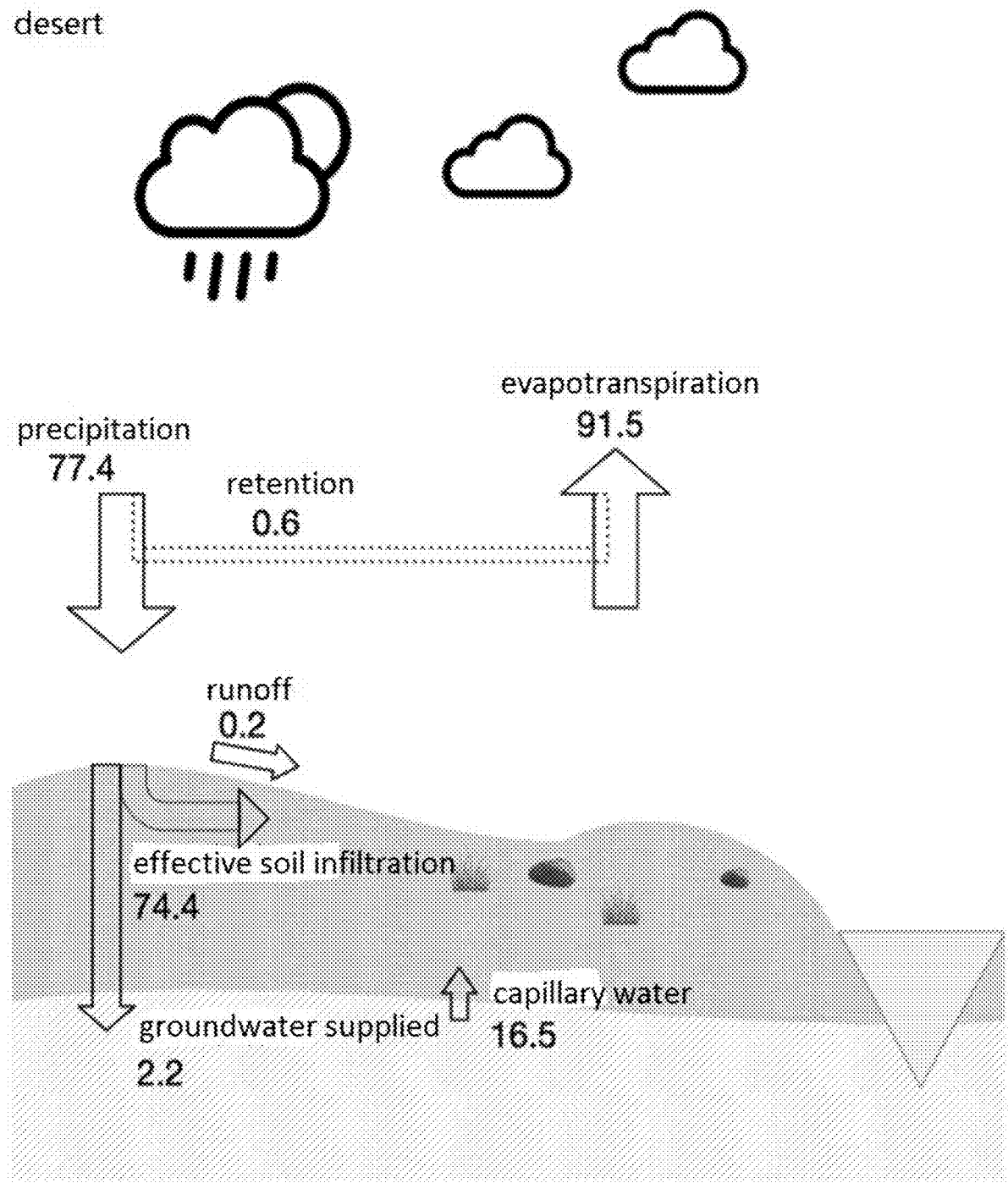
FIG. 8(d) is a schematic diagram of the water circulation in the soil when the soil type of to-be-assessed-area is desert.

On the basis of FIG. 7, the number of the to-be-assessed-areas is 4, for example, when the soil types of the four to-be-assessed-areas are farmland, forest, grassland and desert, the types of water flowing into and out of the soil of the four to-be-assessed-areas and their corresponding water volumes obtained by simulation through the hydrological ecological model are respectively shown as FIG. 8(a)-FIG. 8(d), FIG. 8(a) is a schematic diagram of water circulation in soil when the soil type of to-be-assessed-area is farmland; FIG. 8(b) is a schematic diagram of water circulation in soil when the soil type of to-be-assessed-area is forest; FIG. 8(c) is a schematic diagram of the water circulation in the soil when the soil type of to-be-assessed-area is grassland; FIG. 8(d) is a schematic diagram of the water circulation in the soil when the soil type of to-be-assessed-area is desert. It should be noted that, in this embodiment, the surface runoff flow actually comprises the volume of surface runoff water and the volume of subsurface flow. According to FIG. 8(*a*), the volume of blue water corresponding to the farmland area may be calculated as =442.7+109.4+64.6=616.7; the volume of retention water=442.7+109.4+64.6+(169.8−47.5)−(23.3+7.2)=708.5; thus, the ratio of the volume of blue water to the volume of retention water is 0.87, the corresponding water shortage risk indicator is 0.87, and it can be seen in combination with Table 3 that, the farmland area has an extremly high water shortage risk. The farmland, having a lot of vegetation, consumes a large amount of water, and is high dependent on irrigation, thereby having a high degree of water shortage risk.

According to FIG. 8(*b*), the volume of blue water corresponding to the forest area may be calculated as =171.5+26.7+124.8=323; volume of retention water=171.5+26.7+124.8+(100.9−30.8)−(19.2+10)=363.9; thus, the ratio of the volume of blue water to the volume of retention water is 0.887, the corresponding water shortage risk indicator is 0.887, it can be seen from in combination with Table 3 that, the farmland area has a extremely high water shortage risk. The forest area, with a large amount of vegetation, has a large demand for water, and the green water resource formed by precipitation is not enough to satisfy the demand for soil water, so there is a higher degree of water shortage risk.

According to FIG. 8(*c*), the volume of blue water corresponding to the grassland area may be calculated as =36.2+6.5+53.1=95.8; the volume of retention water=36.2+6.5+53.1+(173.9−41.5)−(30+6.3)=191.9; thus, the ratio of the volume of blue water to the volume of retention water is 0.499, the corresponding water shortage risk indicator is 0.499, it can be seen in combination with Table 3 that, the farmland area has a medium water shortage risk. The grassland area, with most of the vegetation being relatively short, consumes less water than the forest area. And the green water resource in the soil can meet water demand for most of the vegetation.

According to FIG. 8(*d*), the volume of blue water corresponding to the dessert area may be calculated as =0+0+16.5=16.5; the volume of retention water=0+0+16.5+(77.4−0.6)−(0.2+2.2)=90.9; thus, the ratio of the volume of blue water to the volume of retention water is 0.181, the corresponding water shortage risk indicator is 0.181, it can be seen in combination with Table 3 that, the farmland area has a low water shortage risk. With few vegetation, the dessert area has a less demand for water, so the ecological environment of the desert area has a lower degree of water shortage risk.

From the analysis of FIG. 8(*a*) to FIG. 8(*d*), it can be seen that the water shortage risk indicator of the to-be-assessed-area determined according to the ratio of the volume to blue water to the volume of retention water indicates a degree of water shortage risk of the to-be-assessed-area coinciding with that obtained from experience or observation statistics, so the water shortage risk indicator of the to-be-assessed-area determined according to the technical solution of the present application can accurately indicate the degree of the water shortage risk of the ecological environment.

Figure 9A:
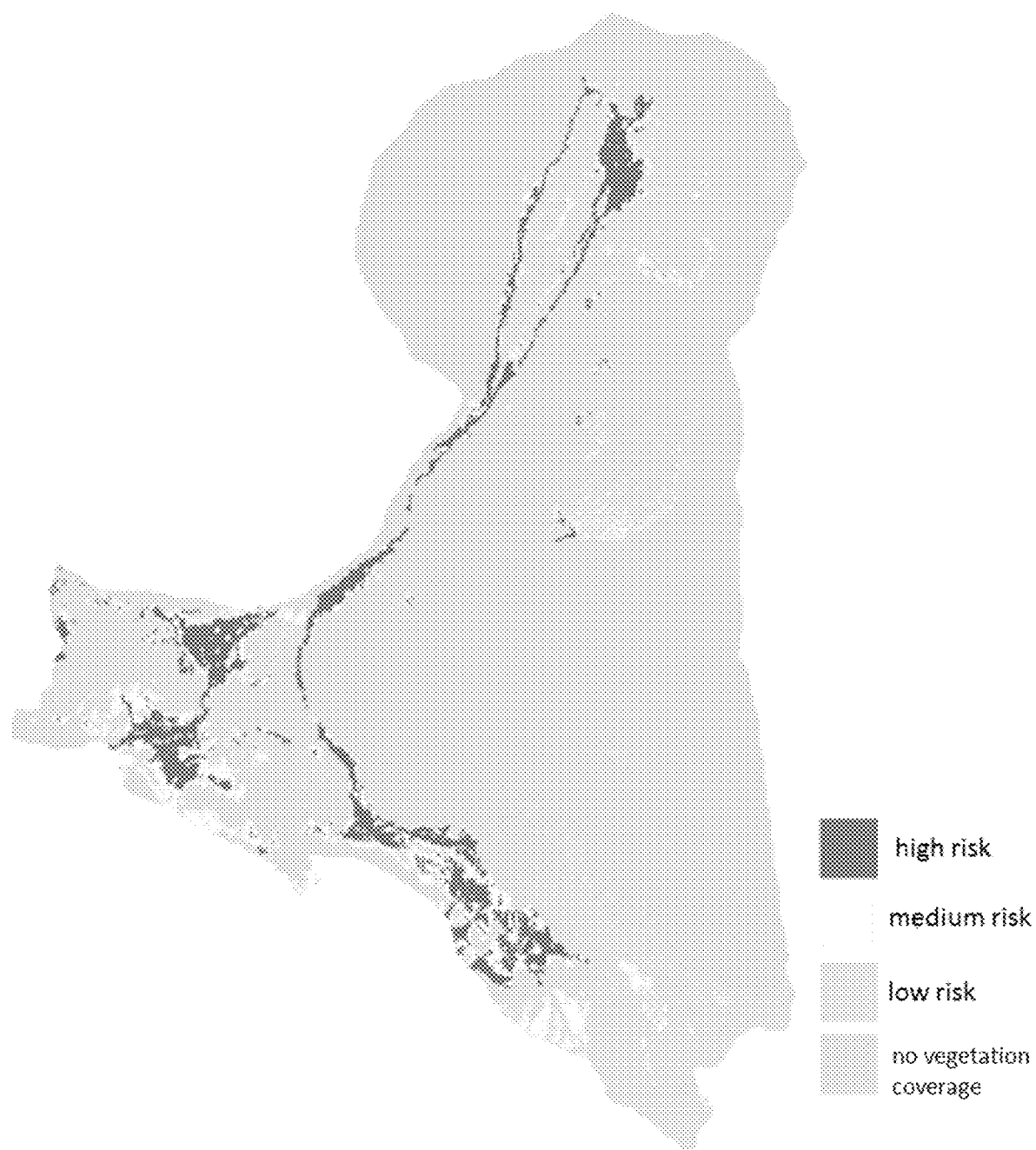
FIG. 9(a) is a schematic diagram of distribution of water shortage risk of each to-be-assessed-area in the Heihe River Basin.
Figure 9B:
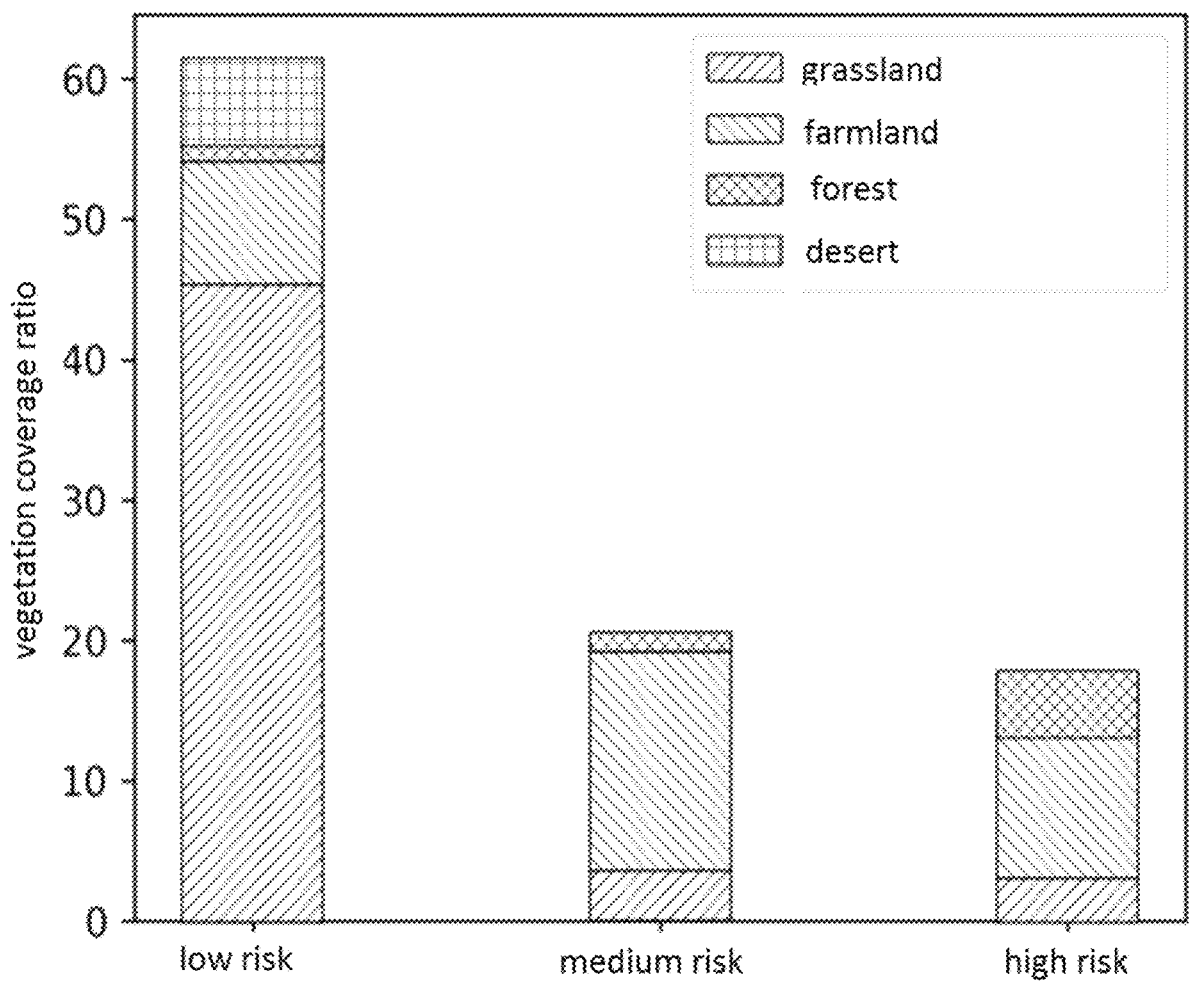
FIG. 9(b) is a schematic diagram of the proportions of different soil types for different water shortage risk indicators.
Figure 9C:
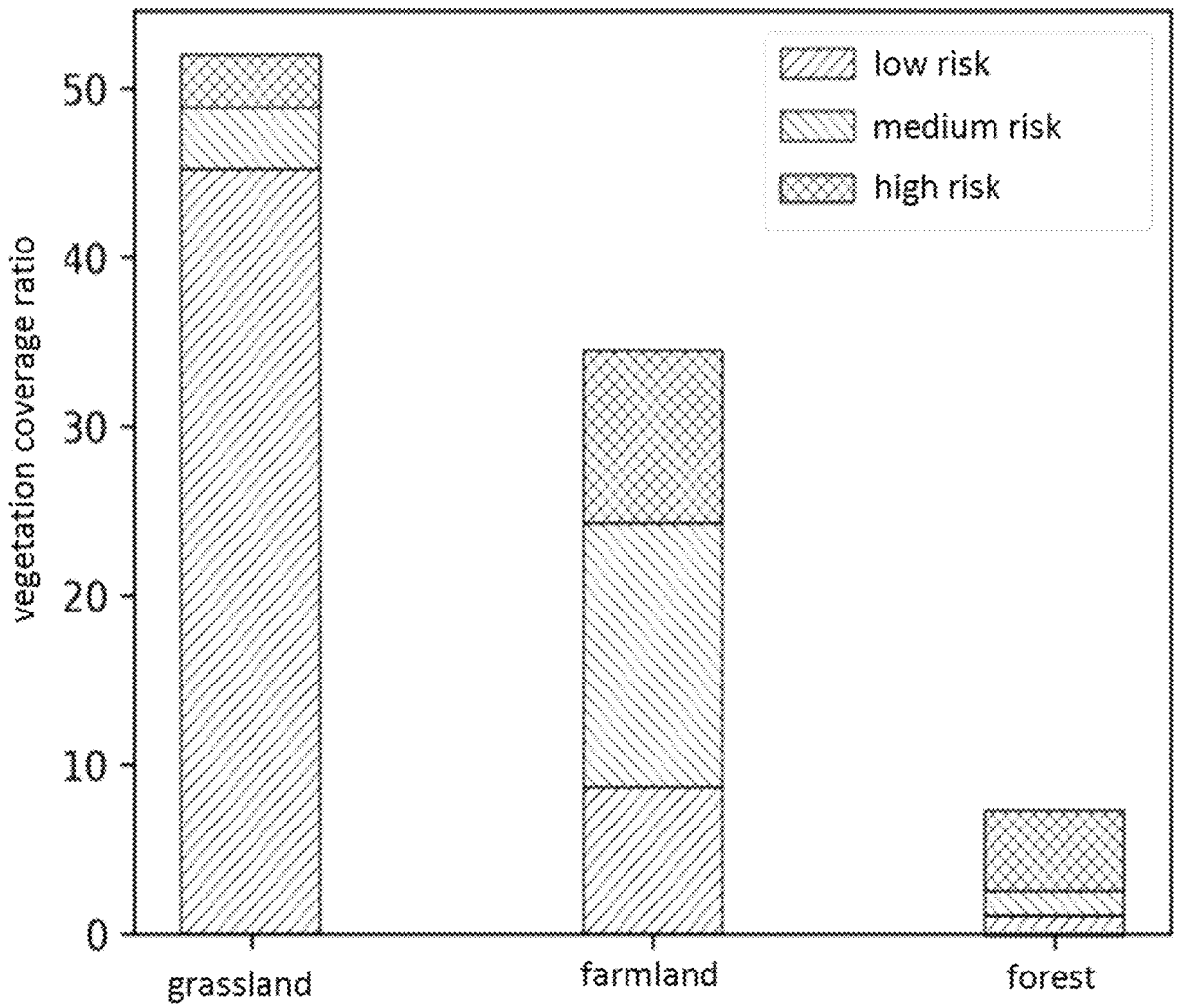
FIG. 9(c) is a schematic diagram of a water shortage risk indicator corresponding to different soil types.

After determining the water shortage risk indicator of the to-be-assessed-area in FIG. 7 based on the methods of FIG. 8(*a*) to FIG. 8(*d*), the water shortage risk indicator of the to-be-assessed-area in the Heihe River Basin may be obtained, specifically shown as FIG. 9(*a*).

On the basis of FIG. 9(*a*), for example, using the vegetation coverage ratio to represent the proportion of the ecological environment, the ratio of each soil type with different water shortage risk indicators may be determined further according to the water shortage risk indicator of each to-be-assessed-area and the vegetation coverage ratio of each to-be-assessed-area, as shown in FIG. 9(*b*), wherein the low risk area accounts for about 62% of the total vegetation coverage area in the Heihe River Basin, and these vegetation coverage areas have a relatively low risk of continuous deterioration in the degree of water resources shortage. This 62% vegetation coverage area comprises about 46% of the grassland ecological environment, about 8% of the farmland ecological environment, about 2% of the forest ecological environment, and about 6% of the desert ecological environment. The medium risk area accounts for about 21% of the total vegetation coverage area in the Heihe River Basin. There is a medium risk of continuous deterioration in the degree of water resources shortage in the vegetation coverage area, comprising about 4% of the grassland ecological environment, about 2% of the forest ecological environment and about 15% of the farmland ecological environment. Similarly, the high risk area accounts for about 17% of the total vegetation coverage area in the Heihe River Basin, comprising about 4% of the grassland ecological environment, about 8% of the farmland ecological environment and about 5% of the forest ecological environment.

On the basis of FIG. 9(*a*), for example, using the vegetation coverage ratio to represent the proportion of the ecological environment, water shortage risk indicators corresponding to different soil types may be determined further according to the soil type of each to-be-assessed-area and the water shortage risk indicator of each to-be-assessed-area, as shown in FIG. 9(*c*), wherein the grassland accounts for 53% of the total vegetation coverage area, most part of which is at low risk, only a small part is at a medium risk and a high risk. The forest accounts for a relatively low proportion of the entire vegetation coverage area, about 7%, but more than 5% of the area in the 7% is at a high risk.

From FIG. 9(*a*)-FIG. 9(*c*), the degree of water shortage risk faced by a certain soil type in the Heihe River Basin, as well as the proportion of the soil with different water shortage risk indicators in the total soil area in the Heihe River Basin may be intuitively learned, which is convenient for water management personnel to allocate water resources in the area reasonably.

Figure 10:
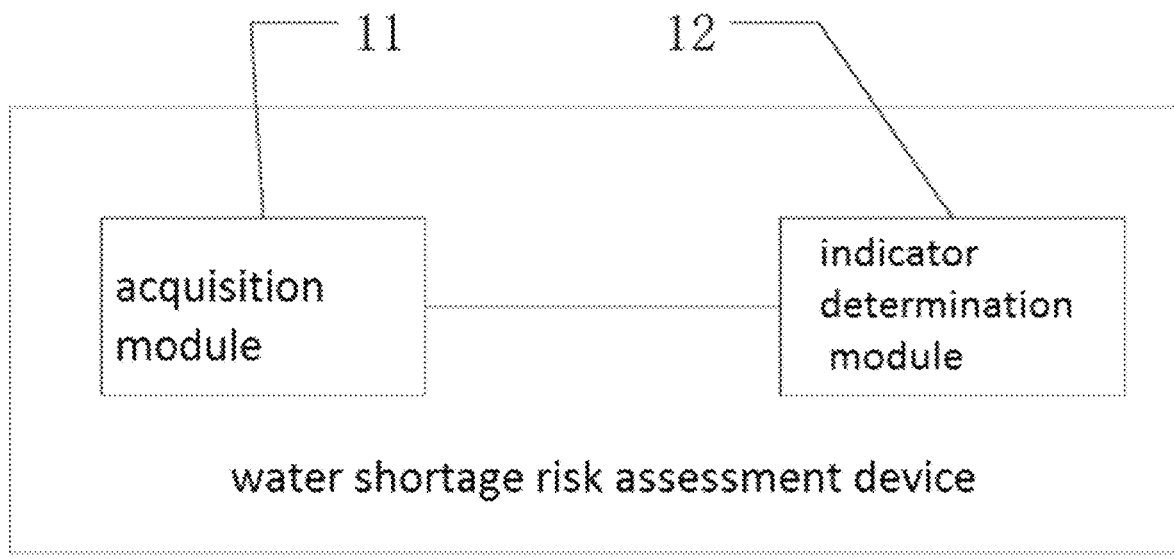
FIG. 10 is a schematic diagram of a water shortage risk assessment device provided by an embodiment.

One embodiment, as shown in FIG. 10, which is a schematic diagram of a water shortage risk assessment device provided by an embodiment, includes: an acquisition module 11, an indicator determination module 12, wherein, the acquisition module 11 is used for acquiring a volume of blue water flowing into soil of a to-be-assessed-area within a target time period, and a volume of retention water flowing into and retained in the soil of the to-be-assessed-area within the target time period; and the indicator determination module 12 is used for determining a water shortage risk indicator of the to-be-assessed-area indicating a degree of water shortage risk of the to-be-assessed-area, according to a ratio of the volume of blue water to the volume of retention water.

In one embodiment, the indicator determination module 12 is specifically used for matching the ratio of the volume of blue water to the volume of retention water with a first mapping relation, and determining the water shortage risk indicator in the to-be-assessed-area, the first mapping relation comprises corresponding relation of different ratio ranges with the water shortage risk indicator.

Figure 11:
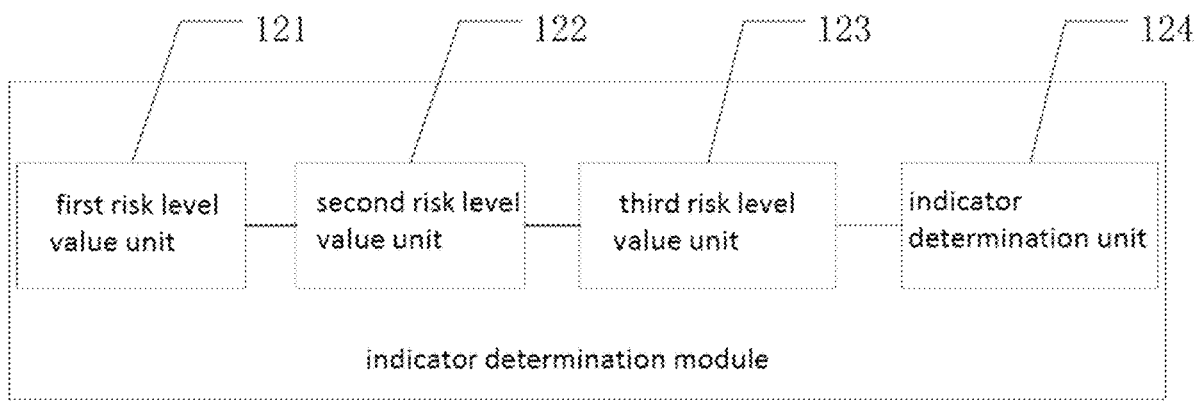
FIG. 11 is a schematic diagram of a water shortage risk assessment device provided by another embodiment.

In one embodiment, as shown in FIG. 11, the indicator determination module 12 comprises:

a first risk level value unit 121, for matching the average per capita water resource in the to-be-assessed-area within a target time period with a second mapping relation, and determining the first risk level value of the to-be-assessed-area; the second mapping relation comprises corresponding relation of different ranges of the average per capita water resource with each risk level value;

a second risk level value unit 122, for matching the ratio of the volume of blue water to the volume of retention water with a third mapping relation, and determining a second risk level value of the to-be-assessed-area, the third mapping relation comprises corresponding relation of different ratio ranges with each risk level value;

a third risk level value unit 123, for calculating a weighted sum of the first risk level value and the second risk level value, to obtain a third risk level value;

an indicator determination unit 124, for matching the third risk level value with a fourth mapping relation, and determining the water shortage risk indicator of the to-be-assessed-area, the fourth mapping relation comprises corresponding relation of different ranges of the risk level value with each water shortage risk indicator.

Figure 12:
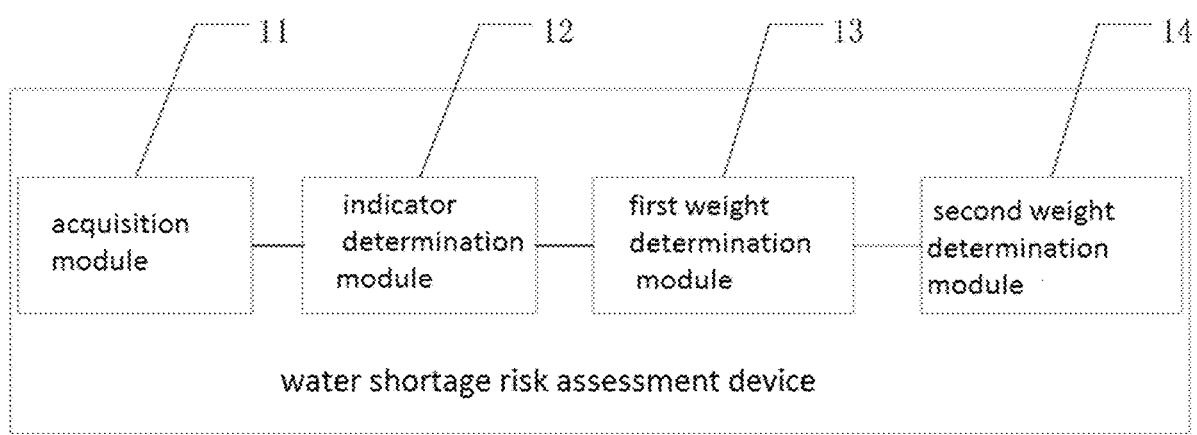
FIG. 12 is a schematic diagram of a water shortage risk assessment device provided by a further embodiment.

In one embodiment, as shown in FIG. 12, the device further comprises:

a first weight determination module 13, for determining a weight Y of the first risk level value using a weight formula Y=aX+b, wherein X represents a total volume of blue water resource in the to-be-assessed-area, a represents slope, b represents intercept; and a second weight determination module 14, for taking an absolute value of a difference between the weight of the first risk level value and 1 as a weight of the second risk level value.

In one embodiment, the indicator determination module 12 is specifically used for taking the ratio of the volume of blue water to the volume of retention water as the water shortage risk indicator of the to-be-assessed-area.

Figure 13:
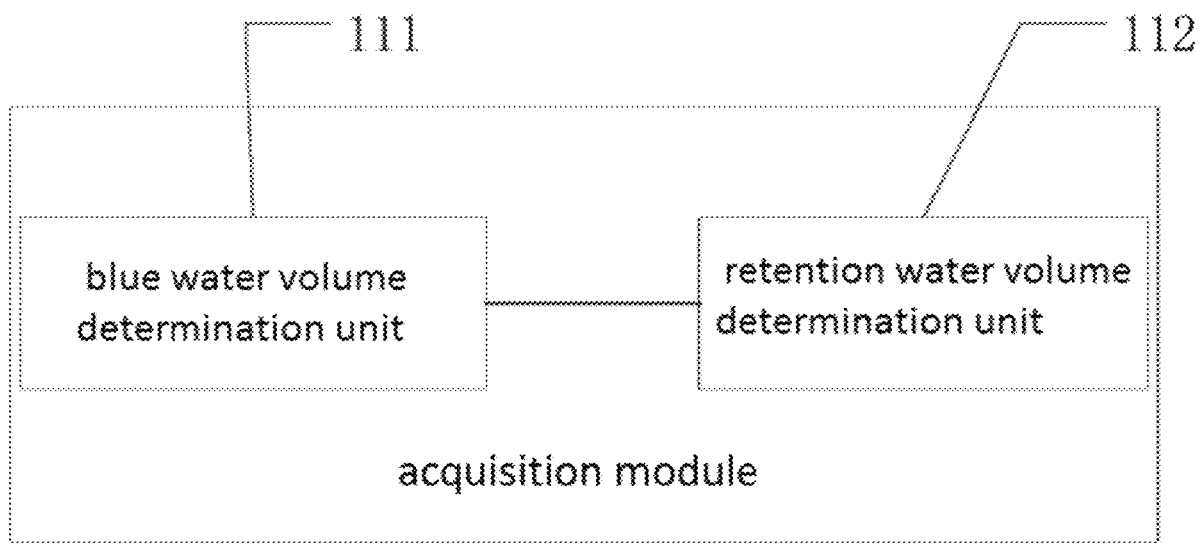
FIG. 13 is a schematic diagram of a water shortage risk assessment device provided by a further embodiment.

In one embodiment, as shown in FIG. 13, the acquisition module 11 comprises:

a volume of blue water determination unit 111, for performing ecological hydrological simulation with an ecological hydrological model, to obtain a simulation result comprising the volume of blue water, the volume of outflow water flowing out of soil in the to-be-assessed-area and volume of vegetation retention water within the target time period; and a volume of retention water determination unit 112, for obtaining the volume of retention water according to precipitation, the volume of vegetation retention water, the volume of blue water and the volume of outflow water within the target time period.

In one embodiment, the acquisition module 11 is further used for taking an average of the volume of blue water corresponding to the multiple target time periods respectively, to obtain an average volume of blue water; and for taking an average volume of retention water corresponding to the multiple target time periods respectively, to obtain an average volume of retention water; and the indicator determination module is specifically used for determining the water shortage risk indicator of the to-be-assessed-area according to a ratio of the average volume of blue water to the average volume of retention water.

For the specific limitation of the water shortage risk assessment device, please refer to the definition of the method for assessing water shortage risk above, which will not be repeated here. Each module in the above water shortage risk assessment device may be wholly or partly realized through software, hardware or combinations thereof. The above modules may be embedded in or independent from the processor in the computer device in the form of hardware, or may be stored in the memory in the computer device in the form of software so that the processor can schedule and execute operations corresponding to the above modules.

In one embodiment, a computer device is provided, comprising memory storing computer programs and a processor, wherein, the processor, when executing the computer program, realizes the following steps:

acquiring a volume of blue water flowing into soil of a to-be-assessed-area within a target time period, and a volume of retention water flowing into and retained in the soil of the to-be-assessed-area within the target time period; and determining a water shortage risk indicator of the to-be-assessed-area indicating a degree of water shortage risk of the to-be-assessed-area, according to a ratio of the volume of blue water to the volume of retention water.

In one embodiment, determining a water shortage risk indicator of the to-be-assessed-area according to a ratio of the volume of blue water to the volume of retention water comprises: matching the ratio of the volume of blue water to the volume of retention water with a first mapping relation, which comprises corresponding relation of different ratio ranges with the water shortage risk indicator, to determine the water shortage risk indicator in the to-be-assessed-area.

In one embodiment, determining a water shortage risk indicator of the to-be-assessed-area according to a ratio of the volume of blue water to the volume of retention water comprises: matching an average per capita water resource in the to-be-assessed-area within the target time period with a second mapping relation, which comprises corresponding relation of different ranges of the average per capita water resource with each risk level value, to determine a first risk level value of the to-be-assessed-area, the second mapping relation; matching the ratio of the volume of blue water to the volume of retention water with a third mapping relation, which comprises corresponding relation of different ratio ranges with each risk level value, to determine a second risk level value of the to-be-assessed-area; calculating a weighted sum of the first risk level value and the second risk level value, to obtain a third risk level value; and matching the third risk level value with a fourth mapping relation, which comprises corresponding relation of different ranges of the risk level value with each water shortage risk indicator, to determine the water shortage risk indicator of the to-be-assessed-area.

In one embodiment, before calculating a weighted sum of the first risk level value and the second risk level value to obtain a third risk level value, the embodiment further comprises: determining a weight Y of the first risk level value using a weight formula Y=aX+b, wherein X represents a total volume of blue water resource in the to-be-assessed-area, a represents slope, b represents intercept; and taking an absolute value of a difference between a weight of the first risk level value and 1 as a weight of the second risk level value.

In one embodiment, determining a water shortage risk indicator of the to-be-assessed-area according to a ratio of the volume of blue water to the volume of retention water comprises taking the ratio of the volume of blue water to the volume of retention water as the water shortage risk indicator of the to-be-assessed-area.

In one embodiment, acquiring a volume of blue water flowing into soil of a to-be-assessed-area within a target time period, and a volume of retention water flowing into and retained in the soil of the to-be-assessed-area within the target time period comprises performing ecological hydrological simulation with an ecological hydrological model, to obtain a simulation result comprising the volume of blue water, a volume of outflow water flowing out of soil in the to-be-assessed-area and a volume of vegetation retention water within the target time period; and obtaining the volume of retention water according to precipitation, the volume of vegetation retention water, the volume of blue water and the volume of outflow water within the target time period.

In one embodiment, the volume of blue water comprises: a volume of irrigation water, a volume of channel leakage and a volume of capillary water.

In one embodiment, the volume of outflow water comprises: a volume of surface runoff water, a volume of groundwater supplied and a volume of subsurface flow.

In one embodiment, the target time period has multiple ones;

before determining a water shortage risk indicator of the to-be-assessed-area according to a ratio of the volume of blue water to the volume of retention water, the embodiment further comprises: taking an average of the volume of blue water corresponding to the multiple target time periods respectively, to obtain an average volume of blue water; taking an average of the volume of retention water corresponding to the multiple target time periods respectively, to obtain an average volume of retention water; and determining a water shortage risk indicator of the to-be-assessed-area according to a ratio of the volume of blue water to the volume of retention water comprises: determining the water shortage risk indicator of the to-be-assessed-area according to a ratio of the average volume of blue water to the average volume of retention water.

In one embodiment, a computer readable storage medium is provided, storing computer program thereon, and the computer program, when executed by the processor, realizes the following steps:

acquiring a volume of blue water flowing into soil of a to-be-assessed-area within a target time period, and a volume of retention water flowing into and retained in the soil of the to-be-assessed-area within the target time period; and determining a water shortage risk indicator of the to-be-assessed-area indicating a degree of water shortage risk of the to-be-assessed-area, according to a ratio of the volume of blue water to the volume of retention water.

In one embodiment, determining a water shortage risk indicator of the to-be-assessed-area according to a ratio of the volume of blue water to the volume of retention water comprises matching the ratio of the volume of blue water to the volume of retention water with a first mapping relation, which comprises corresponding relation of different ratio ranges with the water shortage risk indicator, to determine the water shortage risk indicator in the to-be-assessed-area.

In one embodiment, determining a water shortage risk indicator of the to-be-assessed-area according to a ratio of the volume of blue water to the volume of retention water comprises: matching an average per capita water resource in the to-be-assessed-area within the target time period with a second mapping relation, which comprises corresponding relation of different ranges of the average per capita water resource with each risk level value, to determine a first risk level value of the to-be-assessed-area; matching the ratio of the volume of blue water to the volume of retention water with a third mapping relation, which comprises corresponding relation of different ratio ranges with each risk level value, to determine a second risk level value of the to-be-assessed-area; calculating a weighted sum of the first risk level value and the second risk level value, to obtain a third risk level value; and matching the third risk level value with a fourth mapping relation, which comprises corresponding relation of different ranges of the risk level value with each water shortage risk indicator, to determine the water shortage risk indicator of the to-be-assessed-area.

In one embodiment, before calculating a weighted sum of the first risk level value and the second risk level value to obtain a third risk level value, the embodiment further comprises: determining a weight Y of the first risk level value using a weight formula $Y=aX+b$, wherein X represents a total volume of blue water resource in the to-be-assessed-area, a represents slope, b represents intercept; and taking an absolute value of a difference between a weight of the first risk level value and 1 as a weight of the second risk level value.

In one embodiment, determining a water shortage risk indicator of the to-be-assessed-area according to a ratio of the volume of blue water to the volume of retention water comprises: taking the ratio of the volume of blue water to the volume of retention water as the water shortage risk indicator of the to-be-assessed-area.

In one embodiment, acquiring a volume of blue water flowing into soil of a to-be-assessed-area within a target time period, and a volume of retention water flowing into and retained in the soil of the to-be-assessed-area within the target time period comprises: performing ecological hydrological simulation with an ecological hydrological model, to obtain a simulation result comprising the volume of blue water, a volume of outflow water flowing out of soil in the to-be-assessed-area and a volume of vegetation retention water within the target time period; and obtaining the volume of retention water according to precipitation, the volume of vegetation retention water, the volume of blue water and the volume of outflow water within the target time period.

In one embodiment, the volume of blue water comprises: a volume of irrigation water, a volume of channel leakage and a volume of capillary water.

In one embodiment, the volume of outflow water comprises: a volume of surface runoff water, a volume of groundwater supplied and a volume of subsurface flow.

In one embodiment, the target time period has multiple ones;

before determining a water shortage risk indicator of the to-be-assessed-area according to a ratio of the volume of blue water to the volume of retention water, the method further comprises: taking an average of the volume of blue water corresponding to the multiple target time periods respectively, to obtain an average volume of blue water; taking an average of the volume of retention water corresponding to the multiple target time periods respectively, to obtain an average volume of retention water; and determining a water shortage risk indicator of the to-be-assessed-area according to a ratio of the volume of blue water to the volume of retention water comprises: determining the water shortage risk indicator of the to-be-assessed-area according to a ratio of the average volume of blue water to the average volume of retention water.

The implementation principle and technical effect of the computer readable storage medium provided in the above embodiment are similar to those of the above method embodiment, and will not be repeated here.

Those skilled in the art may understand that all or part of the process in the above method embodiment may be completed by related hardware under instructions from a computer program. The computer program can be stored in a non-volatile computer-readable storage medium. When executed, the computer program can comprise the process of the embodiment of the above methods. Any of the references to memory, storage, database or other media used in the embodiments provided by the present application can comprise non-volatile and/or volatile memory. Non-volatile memory can comprise read-only memory (ROM), programmable ROM (PROM), electrically programmable ROM (EPROM), electrically erasable programmable ROM (EEPROM) or flash memory. Volatile memory can comprise random access memory (RAM) or external cache memory. As an illustration and not a limitation, RANI is available in many forms, such as static RANI (SRAM), dynamic RANI (DRAM), synchronous DRAM (SDRAM), double data rate SDRAM (DDRSDRAM), enhanced SDRAM (ESDRAM), synchronous link (Synchlink) DRAM (SLDRAM), memory bus (Rambus) direct RAM (RDRAM), direct memory bus dynamic RANI (DRDRAM), and memory bus dynamic RANI (RDRAM), etc.

The above technical features of the embodiments may be combined arbitrarily. To simplify the description, not all possible combinations of the technical features in the above embodiments are described. However, as long as there is no contradiction in the combination of these technical features, they should be considered to fall into the scope of the application.

The above embodiments only describe several implementations of the present application, in a specific and detailed way, but it should not be construed as a limitation of the patent scope of the present application. It should be noted that for those of ordinary skill in the art, all modifications and improvements, which may also be made without departing from the idea of the present application, fall into the protection scope of the present application. Therefore, the protection scope of the present application patent shall be defined by the attached claims.

What is claimed is:

1. A method for assessing water shortage risk, comprising:
    acquiring a volume of blue water flowing into soil of a to-be-assessed-area within a target time period, and a volume of retention water flowing into and retained in the soil of the to-be-assessed-area within the target time period; and
    determining a water shortage risk indicator of the to-be-assessed-area indicating a degree of water shortage risk of the to-be-assessed-area, according to a ratio of the volume of blue water to the volume of retention water.

2. The method of claim 1, wherein, determining a water shortage risk indicator of the to-be-assessed-area according to a ratio of the volume of blue water to the volume of retention water comprises:
    matching the ratio of the volume of blue water to the volume of retention water with a first mapping relation, which comprises corresponding relation of different ratio ranges with the water shortage risk indicator, to determine the water shortage risk indicator in the to-be-assessed-area.

3. The method of claim 1, wherein determining a water shortage risk indicator of the to-be-assessed-area according to a ratio of the volume of blue water to the volume of retention water comprises:
    matching an average per capita water resource in the to-be-assessed-area within the target time period with a second mapping relation, which comprises corresponding relation of different ranges of the average per capita water resource with each risk level value, to determine a first risk level value of the to-be-assessed-area;
    matching the ratio of the volume of blue water to the volume of retention water with a third mapping relation, which comprises corresponding relation of different ratio ranges with each risk level value, to determine a second risk level value of the to-be-assessed-area;
    calculating a weighted sum of the first risk level value and the second risk level value, to obtain a third risk level value; and
    matching the third risk level value with a fourth mapping relation, which comprises corresponding relation of different ranges of the risk level value with each water shortage risk indicator, to determine the water shortage risk indicator of the to-be-assessed-area.

4. The method of claim 3, before calculating a weighted sum of the first risk level value and the second risk level value to obtain a third risk level value, further comprising:
    determining a weight Y of the first risk level value using a weight formula $Y=aX+b$, wherein X represents a total volume of blue water resource in the to-be-assessed-area, a represents slope, b represents intercept; and
    taking an absolute value of a difference between a weight of the first risk level value and 1 as a weight of the second risk level value.

5. The method of claim 1, wherein determining a water shortage risk indicator of the to-be-assessed-area according to a ratio of the volume of blue water to the volume of retention water comprises:
    taking the ratio of the volume of blue water to the volume of retention water as the water shortage risk indicator of the to-be-assessed-area.

6. The method of claim 1, wherein acquiring a volume of blue water flowing into soil of a to-be-assessed-area within a target time period, and a volume of retention water flowing into and retained in the soil of the to-be-assessed-area within the target time period comprises:
    performing ecological hydrological simulation with an ecological hydrological model, to obtain a simulation result comprising the volume of blue water, a volume of outflow water flowing out of soil in the to-be-assessed-area and a volume of vegetation retention water within the target time period; and
    obtaining the volume of retention water according to precipitation, the volume of vegetation retention water, the volume of blue water and the volume of outflow water within the target time period.

7. The method of claim 2, wherein acquiring a volume of blue water flowing into soil of a to-be-assessed-area within a target time period, and a volume of retention water flowing into and retained in the soil of the to-be-assessed-area within the target time period comprises:
    performing ecological hydrological simulation with an ecological hydrological model, to obtain a simulation result comprising the volume of blue water, a volume of outflow water flowing out of soil in the to-be-assessed-area and a volume of vegetation retention water within the target time period; and
    obtaining the volume of retention water according to precipitation, the volume of vegetation retention water, the volume of blue water and the volume of outflow water within the target time period.

8. The method of claim 3, wherein acquiring a volume of blue water flowing into soil of a to-be-assessed-area within a target time period, and a volume of retention water flowing into and retained in the soil of the to-be-assessed-area within the target time period comprises:

performing ecological hydrological simulation with an ecological hydrological model, to obtain a simulation result comprising the volume of blue water, a volume of outflow water flowing out of soil in the to-be-assessed-area and a volume of vegetation retention water within the target time period; and obtaining the volume of retention water according to precipitation, the volume of vegetation retention water, the volume of blue water and the volume of outflow water within the target time period.

9. The method of claim 4, wherein acquiring a volume of blue water flowing into soil of a to-be-assessed-area within a target time period, and a volume of retention water flowing into and retained in the soil of the to-be-assessed-area within the target time period comprises:

performing ecological hydrological simulation with an ecological hydrological model, to obtain a simulation result comprising the volume of blue water, a volume of outflow water flowing out of soil in the to-be-assessed-area and a volume of vegetation retention water within the target time period; and obtaining the volume of retention water according to precipitation, the volume of vegetation retention water, the volume of blue water and the volume of outflow water within the target time period.

10. The method of claim 6, wherein, the volume of blue water comprises: a volume of irrigation water, a volume of channel leakage and a volume of capillary water.

11. The method of claim 6, wherein, the volume of outflow water comprises: a volume of surface runoff water, a volume of groundwater supplied and a volume of subsurface flow.

12. The method of claim 6, wherein the target time period has multiple ones;

before determining a water shortage risk indicator of the to-be-assessed-area according to a ratio of the volume of blue water to the volume of retention water, the method further comprises:

taking an average of the volume of blue water corresponding to the multiple target time periods respectively, to obtain an average volume of blue water;

taking an average of the volume of retention water corresponding to the multiple target time periods respectively, to obtain an average volume of retention water; and determining a water shortage risk indicator of the to-be-assessed-area according to a ratio of the volume of blue water to the volume of retention water comprises:

determining the water shortage risk indicator of the to-be-assessed-area according to a ratio of the average volume of blue water to the average volume of retention water.

13. A computer device, comprising memory storing computer programs and a processor, wherein, the processor, when executing the computer program, realizes the method for assessing water shortage risk in claim 1.

14. A water shortage risk assessment device, comprising:

an acquisition module, for acquiring a volume of blue water flowing into soil of a to-be-assessed-area within a target time period, and a volume of retention water flowing into and retained in the soil of the to-be-assessed-area within the target time period; and an indicator determination module, for determining a water shortage risk indicator of the to-be-assessed-area indicating a degree of water shortage risk of the to-be-assessed-area, according to a ratio of the volume of blue water to the volume of retention water.

15. The device of claim 14, wherein, the indicator determination module is specifically used for matching the ratio of the volume of blue water to the volume of retention water with a first mapping relation, and determining the water shortage risk indicator in the to-be-assessed-area, the first mapping relation comprises corresponding relation of different ratio ranges with the water shortage risk indicator.

16. The device of claim 14, wherein the indicator determination module comprises:

a first risk level value unit, for matching an average per capita water resource in the to-be-assessed-area within the target time period with a second mapping relation, and determining a first risk level value of the to-be-assessed-area, the second mapping relation comprises corresponding relation of different ranges of the average per capita water resource with each risk level value;

a second risk level value unit, for matching the ratio of the volume of blue water to the volume of retention water with a third mapping relation, and determining a second risk level value of the to-be-assessed-area, the third mapping relation comprises corresponding relation of different ratio ranges with each risk level value;

a third risk level value unit, for calculating a weighted sum of the first risk level value and the second risk level value, to obtain a third risk level value; and an indicator determination unit, for matching the third risk level value with a fourth mapping relation, and determining the water shortage risk indicator of the to-be-assessed-area, the fourth mapping relation comprises corresponding relation of different ranges of the risk level value with each water shortage risk indicator.

17. The device of claim 16, wherein the device further comprises:

a first weight determination module, for determining a weight Y of the first risk level value using a weight formula Y=aX+b, wherein X represents a total volume of blue water resource in the to-be-assessed-area, a represents slope, b represents intercept; and a second weight determination module, for taking an absolute value of a difference between the weight of the first risk level value and 1 as a weight of the second risk level value.

18. The device of claim 14, wherein, the indicator determination module is specifically used for taking the ratio of the volume of blue water to the volume of retention water as the water shortage risk indicator of the to-be-assessed-area.

19. The device of claim 14, wherein the acquisition module comprises:

a blue water volume determination unit, for performing ecological hydrological simulation with an ecological hydrological model, to obtain a simulation result comprising the volume of blue water, the volume of outflow water flowing out of soil in the to-be-assessed-area and volume of vegetation retention water within the target time period; and a retention water volume determination unit, for obtaining the volume of retention water according to precipitation, the volume of vegetation retention water, the volume of blue water and the volume of outflow water within the target time period.

20. The device of claim 14, wherein, the acquisition module, is further used for taking an average of the volume of blue water corresponding to the multiple target time periods respectively, to obtain an average volume of blue water; and for taking an average volume of retention water corresponding to the multiple target time periods respectively, to obtain an average volume of retention water; and the indicator determination module is specifically used for determining the water shortage risk indicator of the to-be-assessed-area according to a ratio of the average volume of blue water to the average volume of retention water.

* * * * *